US009848965B2

(12) United States Patent
Kim et al.

(10) Patent No.: US 9,848,965 B2
(45) Date of Patent: Dec. 26, 2017

(54) METHOD FOR MANUFACTURING SURGICAL GUIDE AND CROWN, ABUTMENT IN MOUTH FOR DENTAL IMPLANT

(71) Applicant: DIO Corporation, Busan (KR)

(72) Inventors: Jin Chul Kim, Yangsan-si (KR); Jin Baek Kim, Busan (KR); Byung Ho Choi, Wonju-si (KR); Seung Mi Jung, Wonju-si (KR)

(73) Assignee: DIO CORPORATION, Busan (KR)

( * ) Notice: Subject to any disclaimer, the term of this patent is extended or adjusted under 35 U.S.C. 154(b) by 104 days.

(21) Appl. No.: 14/851,116

(22) Filed: Sep. 11, 2015

(65) Prior Publication Data
US 2016/0157967 A1 Jun. 9, 2016

(30) Foreign Application Priority Data

| Dec. 5, 2014 | (KR) | 10-2014-0174007 |
| Mar. 3, 2015 | (KR) | 10-2015-0029756 |
| Mar. 9, 2015 | (KR) | 10-2015-0032445 |
| Apr. 6, 2015 | (KR) | 10-2015-0048380 |

(51) Int. Cl.
| *A61C 13/00* | (2006.01) |
| *A61C 1/08* | (2006.01) |
| *A61B 6/03* | (2006.01) |
| *A61B 6/14* | (2006.01) |
| *A61C 8/00* | (2006.01) |
| *A61C 13/271* | (2006.01) |
| *A61C 9/00* | (2006.01) |
| *A61C 19/05* | (2006.01) |

(Continued)

(52) U.S. Cl.
CPC .......... *A61C 13/0004* (2013.01); *A61B 6/032* (2013.01); *A61B 6/14* (2013.01); *A61C 1/084* (2013.01); *A61C 5/70* (2017.02); *A61C 5/77* (2017.02); *A61C 8/005* (2013.01); *A61C 8/0048* (2013.01); *A61C 9/004* (2013.01); *A61C 9/0006* (2013.01); *A61C 13/26* (2013.01);
(Continued)

(58) Field of Classification Search
CPC ......... A61C 1/084; A61C 1/082; A61C 9/004; A61C 9/0053; A61C 8/00; A61C 8/006; A61C 8/0089; A61B 90/39
USPC ............................. 433/75, 76, 172, 213, 214
See application file for complete search history.

(56) References Cited

U.S. PATENT DOCUMENTS

| 8,944,818 B2 * | 2/2015 | Robb | A61C 8/008 433/172 |
| 2003/0219148 A1 * | 11/2003 | Scharlack | A61C 1/084 382/128 |

(Continued)

*Primary Examiner* — Nicholas Lucchesi
(74) *Attorney, Agent, or Firm* — Paratus Law Group, PLLC

(57) ABSTRACT

Provided is a method for manufacturing a surgical guide, and a crown and an abutment in a mouth for a dental implant, including an operation of obtaining a primarily scanned image through scanning of inner and outer surfaces of a denture which has a first image matching groove matched with a patient's tooth implanting portion and in which a plurality of reference markers are attached to an outside, obtaining a secondarily scanned image through oral scanning of upper and lower jaws while the denture is installed, preliminarily matching the secondarily scanned image with the primarily scanned image, obtaining an integrated scanned image considering a vertical dimension by reversing the first image matching groove so that an image of the first image matching groove is dimensionalized from the primarily scanned image, and obtaining a CT image through CT scanning of the upper and lower jaws.

10 Claims, 19 Drawing Sheets

(51) Int. Cl.
*A61C 5/70* (2017.01)
*A61C 5/77* (2017.01)
*A61B 90/00* (2016.01)

(52) U.S. Cl.
CPC ...... *A61C 19/05* (2013.01); *A61B 2090/3966* (2016.02); *A61C 2201/005* (2013.01)

(56) References Cited

U.S. PATENT DOCUMENTS

| | | | |
|---|---|---|---|
| 2004/0029068 A1* | 2/2004 | Sachdeva | A61C 7/00 433/24 |
| 2009/0011382 A1* | 1/2009 | Bavar | A61C 1/084 433/76 |
| 2009/0316966 A1* | 12/2009 | Marshall | A61B 6/5217 382/128 |
| 2010/0255445 A1* | 10/2010 | Gantes | A61C 1/084 433/173 |
| 2011/0008751 A1* | 1/2011 | Pettersson | A61C 1/084 433/167 |
| 2013/0337400 A1* | 12/2013 | Yi | A61B 6/14 433/25 |
| 2014/0186796 A1* | 7/2014 | Suttin | A61C 8/0001 433/172 |
| 2014/0205969 A1* | 7/2014 | Marlin | A61C 8/0001 433/173 |
| 2014/0379356 A1* | 12/2014 | Sachdeva | A61C 7/002 705/2 |
| 2015/0209118 A1* | 7/2015 | Kopelman | A61B 19/54 433/25 |

* cited by examiner

METHOD FOR MANUFACTURING SURGICAL GUIDE AND CROWN, ABUTMENT IN MOUTH FOR DENTAL IMPLANT

CROSS-REFERENCE TO RELATED APPLICATION

This application claims the benefit of Korean Application No. 10-2014-174007 which was filed on Dec. 5, 2014, and Korean Application No. 10-2015-29756 which was filed on Mar. 3, 2015, and Korean Application No. 10-2015-32445 which was filed on Mar. 9, 2015, and Korean Application No. 10-2015-48380 which was filed on Apr. 6, 2015, which were hereby incorporated by references as if fully set forth herein.

BACKGROUND

1. Field of the Invention

The present invention relates to a dental implant, and more particularly, to a method for manufacturing a surgical guide, and a crown and an abutment in a mouth for a dental implant, which precisely obtains an image of an inside of a patient's mouth, and thus enhances accuracy of the dental implant.

2. Discussion of Related Art

Generally, an implant is a substitute for a part of a human organism, when the part of the human organism is lost. However, in the field of dentistry, an implant means that an artificial tooth is implanted.

Specifically, in the case of a prosthetic appliance or a denture, other teeth and bones therearound are damaged, as time goes on. However, the implant may prevent peripheral dental tissues from being damaged, does not have secondary dental caries production factors, and thus may be safely used. Also, since the implant has a structure corresponding to a natural tooth, there are little pain in the gum region and little feeling of irritation, and it may be semipermanently used, if it is maintained well.

Meanwhile, in a dental implant, a hole is formed at an alveolar bone using a drill, and a fixture is implanted in the hole. A procedure of forming the hole and a procedure of implanting the fixture may be varied according to patients. This is because implantation position, depth and direction of the dental implant should be determined in consideration of various factors such as patient's dental conditions, a position of a tooth to be treated by the dental implant, and conditions of a patient's alveolar bone.

Meanwhile, in a drilling operation for forming the hole at the alveolar bone, it is very difficult for not only an inexperienced dentist but also a skilled dentist to accurately estimate a depth and a direction during the operation.

Further, when a drill is inserted to more than a predetermined depth, there may be a serious problem in that a nerve of the alveolar bone may be damaged. On the contrary to this, when the drilling operation is terminated before reaching the predetermined depth, an excessive force is required to fix the fixture due to a shallow depth of the formed hole. Also, there may be other problems in that a screw thread around the hole is damaged, or the fixture is not completely fixed, and thus a reoperation is required later.

Therefore, an aid tool referred to as a surgical guide is used to grasp an accurate position and direction for performing the drilling operation.

Meanwhile, FIG. 1 is a flowchart illustrating a method for manufacturing a conventional surgical guide.

As illustrated in FIG. 1, in the conventional surgical guide, a three-dimensional image of an inside of a patient's mouth is obtained through CT scanning, and a three-dimensional exterior image of the inside of the patient's mouth is obtained through oral scanning (s1).

Here, the three-dimensional image obtained through the CT scanning includes internal tissue information of shapes of a crown, a tooth root and an alveolar bone, and bone densities thereof. Also, the three-dimensional external shape image obtained through the oral scanning includes exterior information of the crown and a gum in the mouth.

When each image is obtained, the two images are matched with each other based on a point in the mouth set by an operator (s2). Then, a dental implant plan is established through an image matching result (s3), and the surgical guide which may guide a procedure according to the dental implant plan is manufactured (s4).

Here, it is preferable that the surgical guide be manufactured using external shape data of oral tissues together, rather than using only the three-dimensional image through the CT scanning.

Specifically, the three-dimensional external shape image is obtained by combining information scanned while an oral scanner is moved along the inside of the patient's mouth, and includes overall shapes of the crown of the tooth and the gum. However, in a process in which the scanned information is combined, a curvature of a tooth arrangement may be indicated in a distorted state which is different from an actual inside of the mouth, and thus an image correction process is required. Like this, to supply scarce information and to correct distorted information in each image, an image matching process in which the two images are matched with each other is necessarily required.

Here, a common portion between the two images, such as a crown region, is needed to match the three-dimensional image with the three-dimensional external shape image. However, in the case of an edentulous patient, since the crown region is lost, it is substantially difficult that the common portion between the three-dimensional image and the three-dimensional external shape image exists. Therefore, there are some problems in that it is difficult to match the images, and even though the images are matched with each other, inaccurate information is included in a matched image.

Also, when a lower jaw in the mouth is edentulous, the exposed gum region is increased, and movement tissues such as a tongue are distributed, and movability of the tissues is increased, and thus it is difficult for a scanned image to be clearly specified. Therefore, there is a problem in that it is difficult to obtain a precise external shape through the oral scanning.

Also, even when a reference marker used as a reference point of the image matching is provided at the inside of the mouth, there is another problem in that the reference marker is not substantially fixed due to the movability of the tissues. Therefore, in the image matching process, even though the images are matched with each other using the reference marker as a matching reference point, reliability of the obtained image is lowered.

Meanwhile, when a crown of the implant for replacing a lost tooth in the patient's mouth is designed, a height, a width, a masticating surface and a masticating direction of the crown are calculated based on information of teeth remaining around the lost tooth. However, in the case of the edentulous patient, since there are not the peripheral teeth as comparable objects, the crown is designed through operator's experience or existing procedure data.

However, when such manufactured crown is implanted in the patient's mouth, the patient often feels uncomfortable. Also, since a plurality of crowns should be manufactured, and the implanting process should be repeated to correct the discomfort, a procedure cost is increased. Thus, a period of time for the dental plant is extended, and it causes patient's inconvenience.

SUMMARY OF THE INVENTION

The present invention is directed to a method for manufacturing a surgical guide, and a crown and an abutment in a mouth for a dental implant, which precisely obtains an image of an inside of a patient's mouth, and thus enhances accuracy of the dental implant.

According to an aspect of the present invention, there is provided a method for manufacturing a surgical guide, and a crown and an abutment in a mouth for a dental implant, including a first operation of obtaining a primarily scanned image through scanning of inner and outer surfaces of a denture which has a first image matching groove matched with a patient's tooth implanting portion and in which a plurality of reference markers are attached to an outside thereof, obtaining a secondarily scanned image through oral scanning of upper and lower jaws while the denture is installed, preliminarily matching the secondarily scanned image with the primarily scanned image, obtaining an integrated scanned image considering a vertical dimension by reversing the first image matching groove so that an image of the first image matching groove is dimensionalized from the primarily scanned image, and obtaining a CT image through CT scanning of the upper and lower jaws; a second operation of obtaining a three-dimensional occlusion guide image by overlapping the obtained integrated scanned image with the obtained CT image using the reference markers as references and matching the images through a main snatching process in a difference map from which an image matching degree between the images is output; and a third operation of setting a height of a crown based on the three-dimensional occlusion guide image, and manufacturing a surgical guide including a fixing groove matched with an internal shape of the patient's mouth and a guide hole formed along an implanting position of a fixture corresponding to the set crown.

According to another aspect of the present invention, there is provided a method for manufacturing a surgical guide, and a crown and an abutment in a mouth for a dental implant, including a first operation of coupling a tray, in which a plurality of reference markers are attached to a side surface thereof and an impression material is injected to an inner surface thereof, to an inside of a patient's mouth, and thus taking an impression having a second image matching groove corresponding to a tooth implanting portion; a second operation of obtaining a primarily scanned image through scanning of the tray in which an occlusal height is set by stacking an occlusal base on an outer surface thereof and adjusting a thickness thereof, obtaining a secondarily scanned image through oral scanning of an occluded state of upper and lower jaws while the tray is installed, preliminarily matching the secondarily scanned image with the primarily scanned image, obtaining an integrated scanned image considering a vertical dimension by reversing the second image matching groove so that an image of the second image matching groove is dimensionalized from the primarily scanned image, and obtaining an CT image through CT scanning of the upper and lower jaws; a third operation of obtaining a three-dimensional occlusion guide image by overlapping the obtained integrated scanned image with the obtained CT image using the reference markers as references and matching the images through a main matching process in a difference map from which an image matching degree between the images is output; and a fourth operation of setting a height of a crown based on the three-dimensional occlusion guide image, and manufacturing a surgical guide including a fixing groove matched with an internal shape of the patient's mouth and a guide hole formed along an implanting position of a fixture corresponding to the set crown.

According to still another aspect of the present invention, there is provided a method for manufacturing a surgical guide, and a crown and an abutment in a mouth for a dental implant, including a first operation of obtaining a primarily scanned image by attaching a plurality of reference markers to an outside of a first impression model manufactured corresponding to a patient's tooth implanting portion and then scanning the first impression model; a second operation of inserting the reference markers into marker grooves of a splint which is manufactured by being three-dimensionally printed to protrude from a tooth implanting portion area surface of the primarily scanned image to an outside, such that an inner surface thereof corresponds to the tooth implanting portion and includes the marker grooves matched with the reference markers, and stacking an occlusal base on an outer surface of the splint opposed to an opposing tooth; a third operation of obtaining a CT image through CT scanning of a state that the splint in which an occlusal height is set by adjusting a thickness of the occlusal base is installed at the tooth implanting portion; a fourth operation of obtaining a three-dimensional occlusion guide image by overlapping the primarily scanned image with the CT image using the reference markers as references and matching the images through a main matching process in a difference map from which an image matching degree between the images is output; and a fifth operation of setting a height of a crown based on the three-dimensional occlusion guide image, and manufacturing a surgical guide including a fixing groove matched with an internal shape of the patient's mouth and a guide hole formed along an implanting position of a fixture corresponding to the set crown.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, a method for manufacturing a surgical guide, and a crown and an abutment in a mouth for a dental implant according to the present invention will be described in detail with reference to the accompanying drawings.

Figure 1:
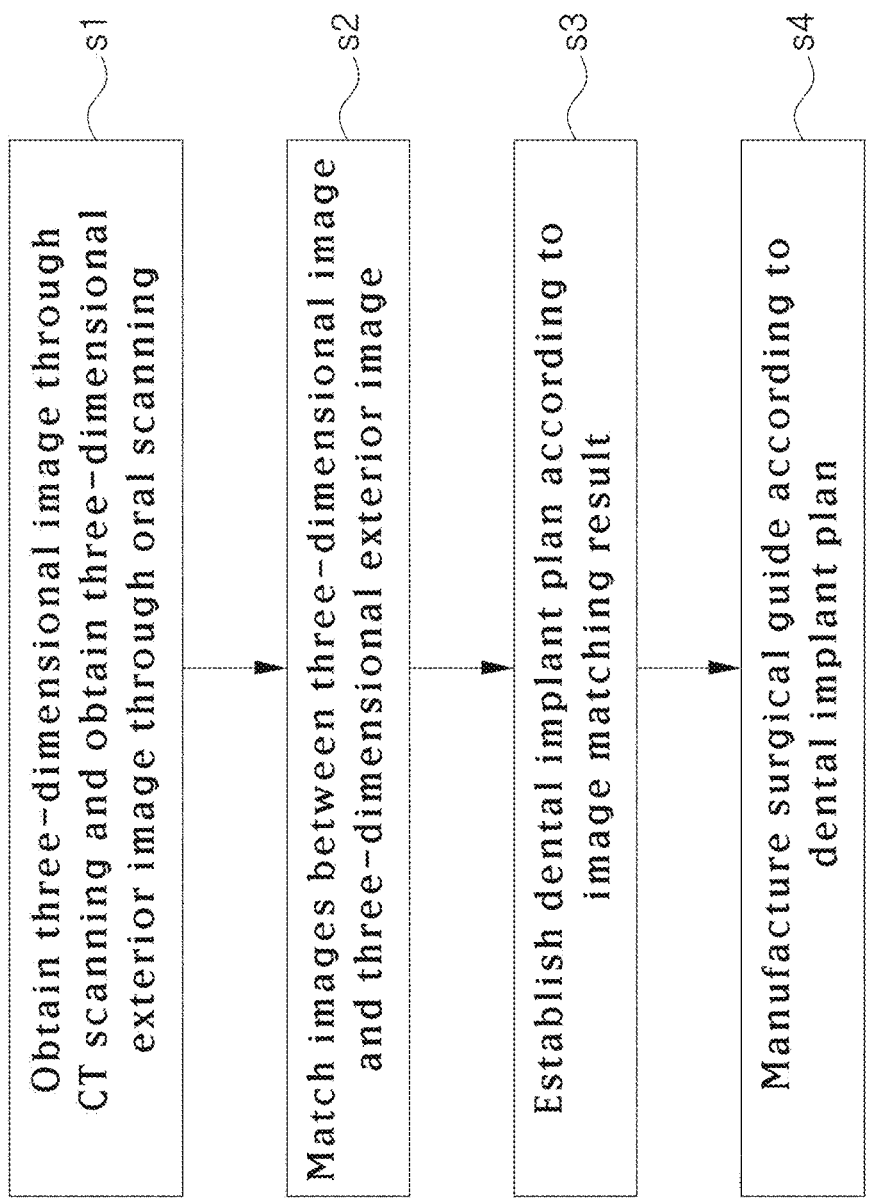
FIG. 1 is a flowchart illustrating a method of manufacturing a conventional surgical guide.
Figure 2:
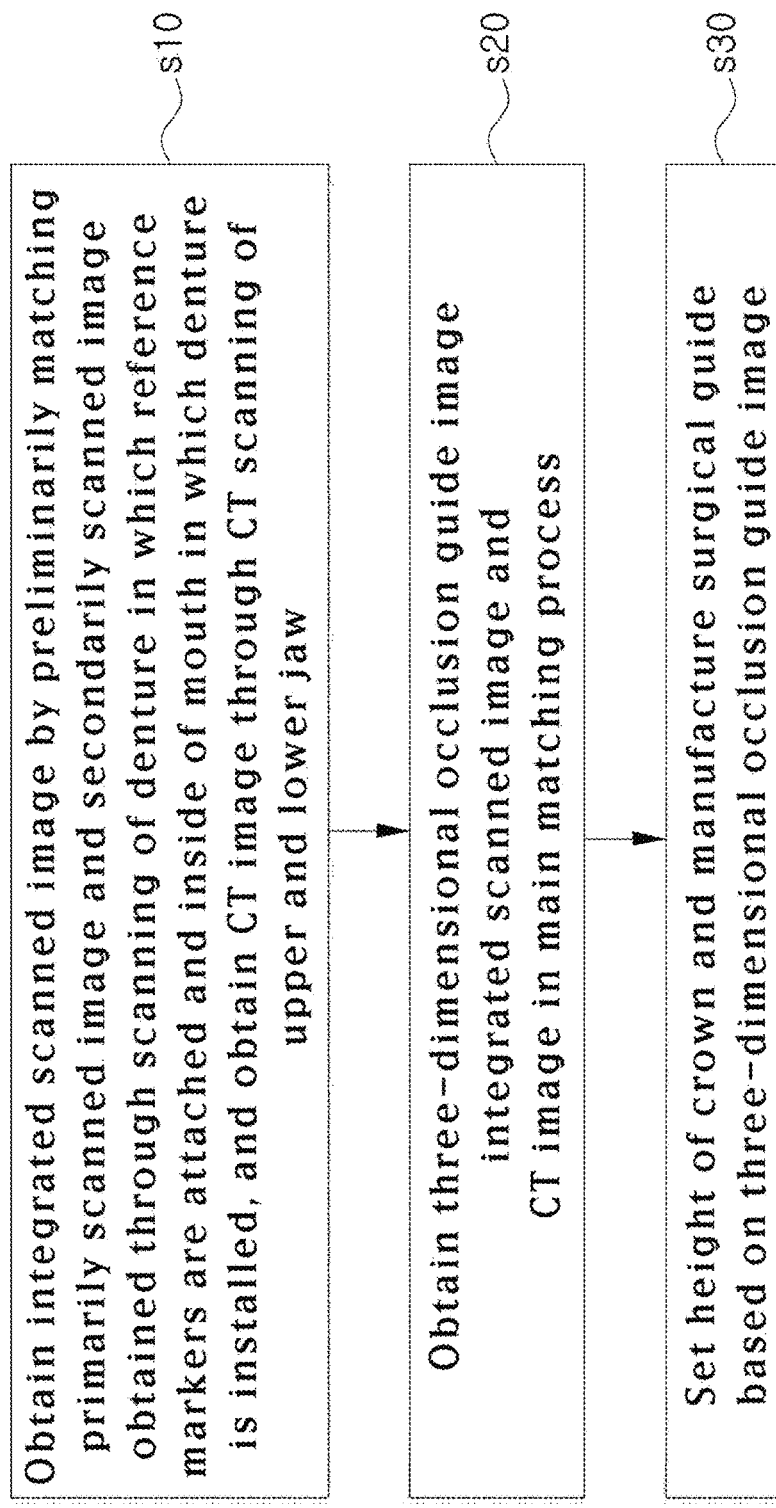
FIG. 2 is a flowchart illustrating a method for manufacturing a surgical guide, and a crown and an abutment in a mouth for a dental implant according to a first embodiment of the present invention.
Figure 3:
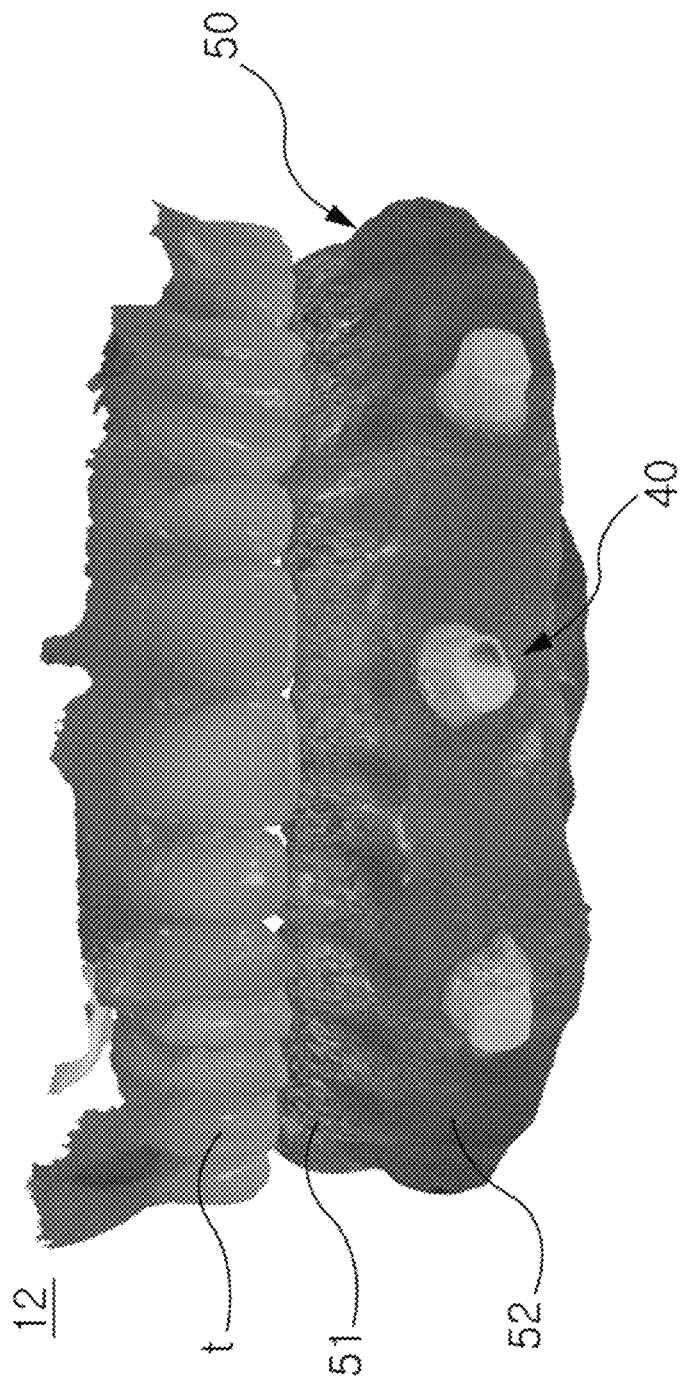
FIG. 3 is an exemplary view illustrating a secondarily scanned image according to the first embodiment of the present invention.
Figure 4:
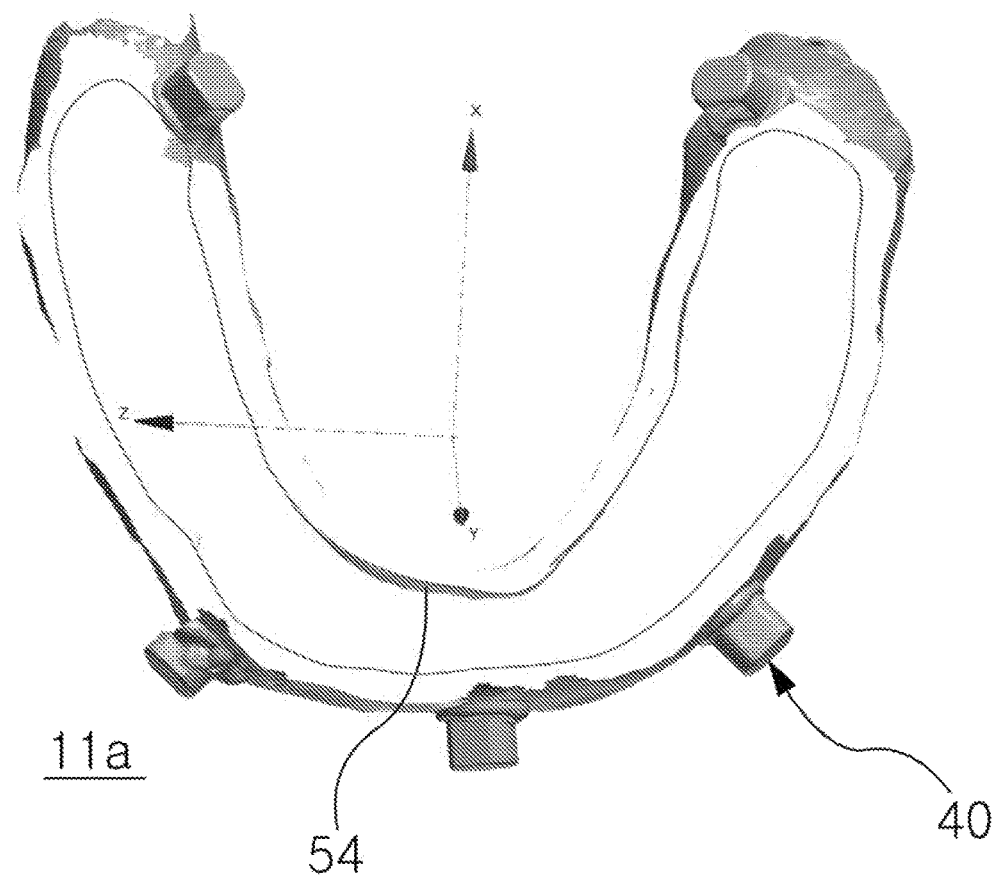
FIG. 4 is an exemplary view illustrating a reversing process for dimensionalizing an image matching groove in a primarily scanned image according to the first embodiment of the present invention.
Figure 5:
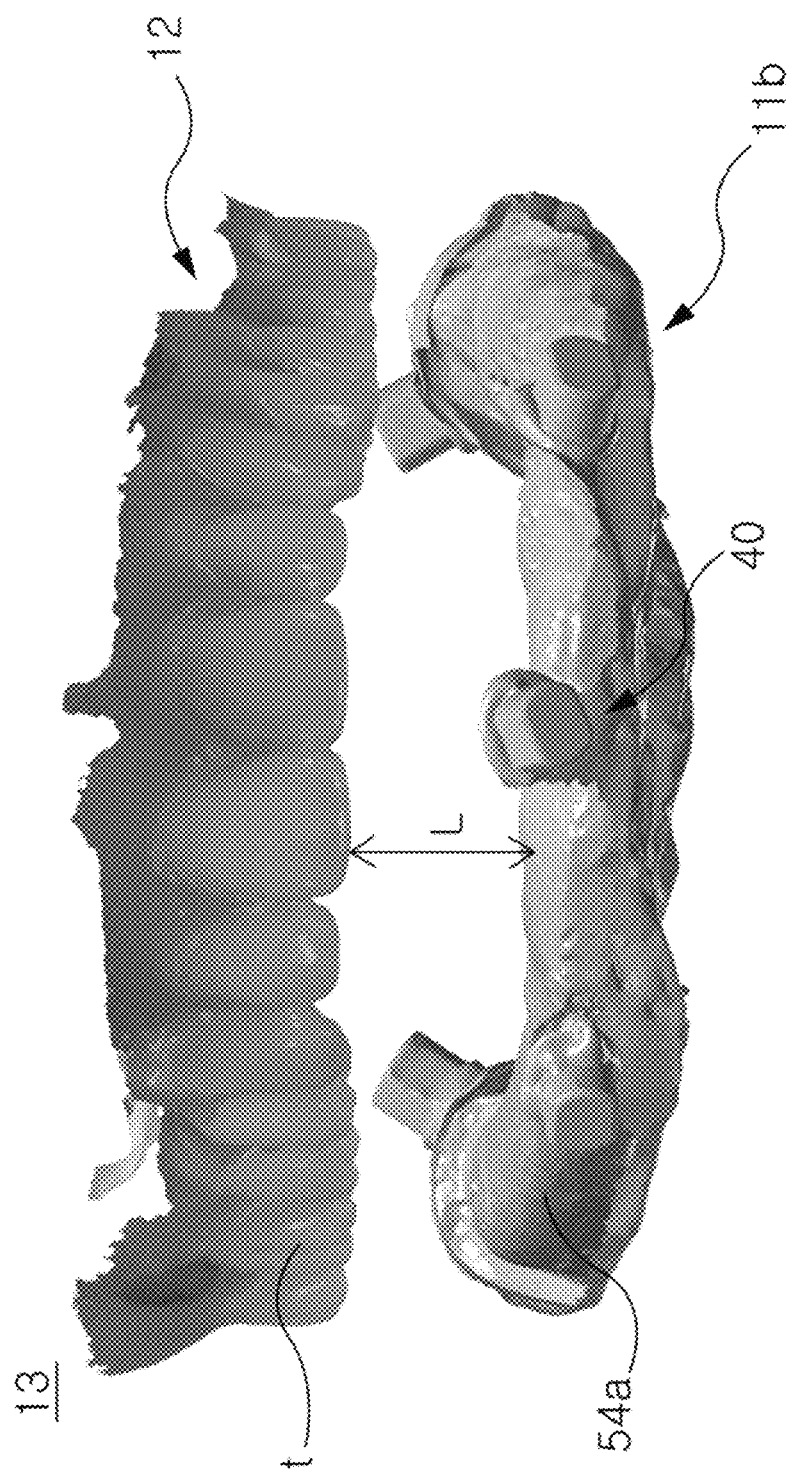
FIG. 5 is an exemplary view illustrating an integrated scanned image considering a vertical dimension according to the first embodiment of the present invention.
Figure 6:
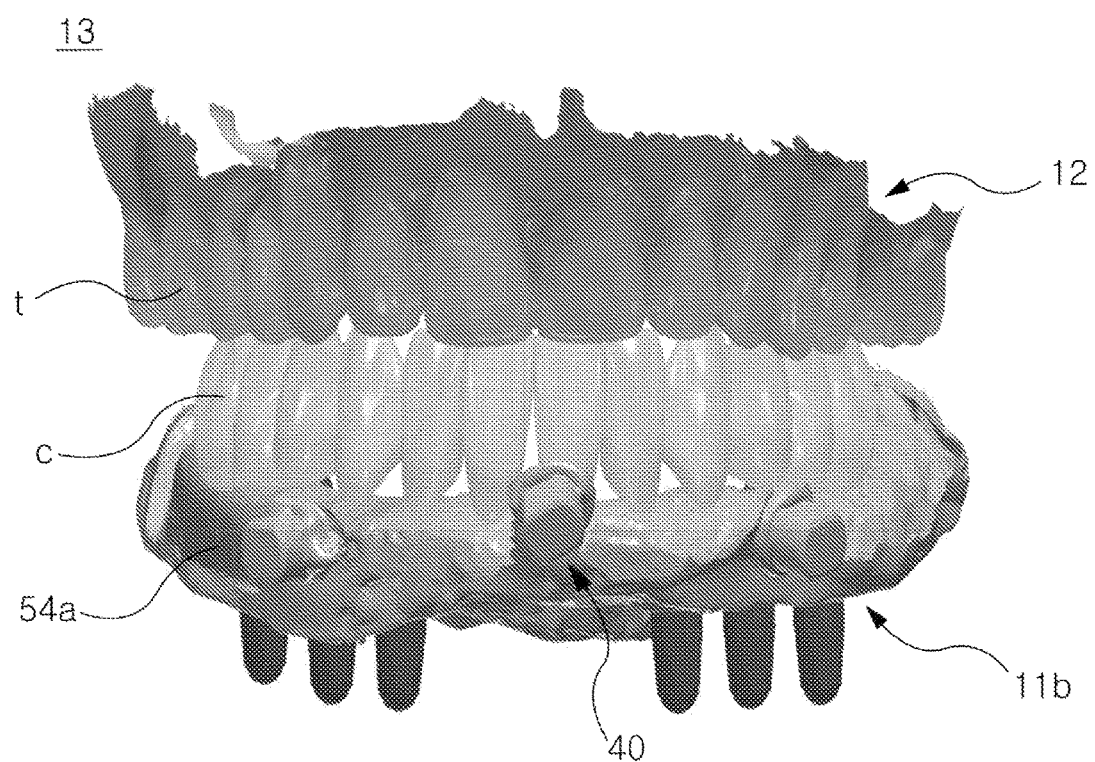
FIG. 6 is an exemplary view illustrating a crown image in the integrated scanned image considering the vertical dimension according to the first embodiment of the present invention.
Figure 7:
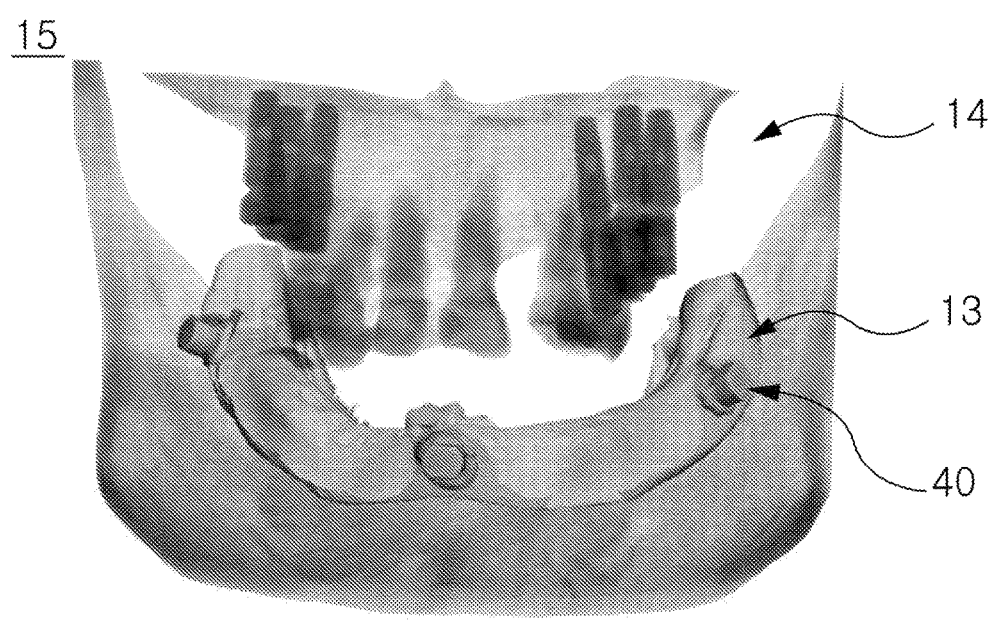
FIG. 7 is an exemplary view illustrating a three-dimensional occlusion guide image according to the first embodiment of the present invention.
Figure 8:
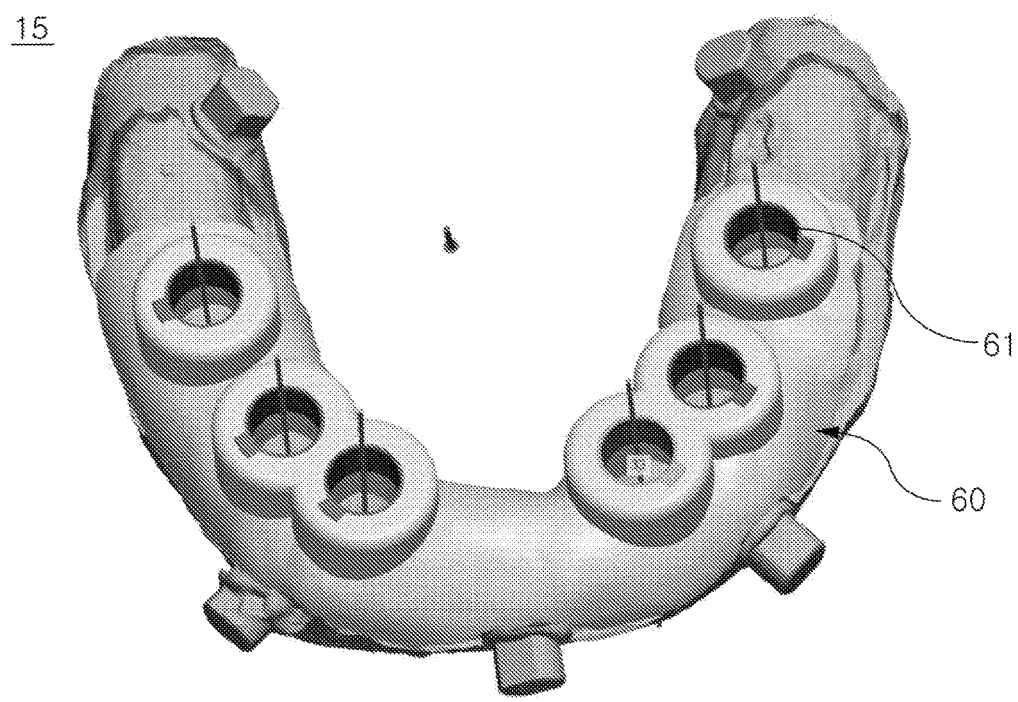
FIG. 8 is an exemplary view illustrating a state in which a surgical guide is designed from the three-dimensional occlusion guide image according to the first embodiment of the present invention.

FIG. 2 is a flowchart illustrating a method for manufacturing a surgical guide, and a crown and an abutment in a mouth for a dental implant according to a first embodiment of the present invention, and FIG. 3 is an exemplary view illustrating a secondarily scanned image according to the first embodiment of the present invention. FIG. 4 is an exemplary view illustrating a reversing process for dimensionalizing an image matching groove in a primarily scanned image according to the first embodiment of the present invention, and FIG. 5 is an exemplary view illustrating an integrated scanned image considering a vertical dimension according to the first embodiment of the present invention. FIG. 6 is an exemplary view illustrating a crown image in the integrated scanned image considering the vertical dimension according to the first embodiment of the present invention, and FIG. 7 is an exemplary view illustrating a three-dimensional occlusion guide image according to the first embodiment of the present invention. And FIG. 8 is an exemplary view illustrating a state in which a surgical guide is designed from the three-dimensional occlusion guide image according to the first embodiment of the present invention.

Meanwhile, in the dental implant, a hole is formed at an alveolar bone using a drill, and a fixture is implanted in the hole. At this time, an aid tool referred to as a surgical guide is used to grasp an accurate position and direction for performing a drilling operation.

Specifically, as illustrated in FIGS. 2 to 8, the method for manufacturing the surgical guide, and the crown and the abutment in the mouth for the dental implant according to the first embodiment of the present invention proceeds as follows. At this time, the method for manufacturing the surgical guide, and the crown and the abutment in the mouth for the dental implant may be applied to a dental implant of a patient whose at least one of upper jaw and lower jaw is edentulous.

Here, it may be understood that an implantation material in the dental implant includes a fixture which replaces a tooth root, a crown which replaces a crown, and an abutment which connects between the fixture and the crown. Also, manufacturing of the implantation material includes manufacturing of the crown corresponding to a tooth arrangement and a vertical dimension of a patient, and may also include selecting of the fixture and the abutment standardized corresponding to patient's bone tissues. Of course, if necessary, the abutment may be separately manufactured corresponding to the patient's tooth arrangement.

Meanwhile, a primarily scanned image is obtained through scanning of an inner surface and an outer surface of a denture 50 in which a first image matching groove 54 which is matched with a tooth implanting portion of the patient s formed, and a plurality of reference markers 40 are attached to an outside thereof. Also, a secondarily scanned image 12 is obtained through oral scanning of upper and lower jaws, while the denture 50 is installed. The primarily scanned image and the secondarily scanned image 12 are preliminarily matched with each other. At this time, an integrated scanned image 13 considering the vertical dimension is obtained by reversing the first image matching groove 54 on the preliminarily matched image to dimensionalize an image of the first image matching groove 54 from the primarily scanned image. That is, the first image matching groove 54 is reversed so that the concave image of the first image matching groove 54 included in the primarily scanned image is convexly dimensionalized on the above-described overlapped image. Consequently, the first image matching groove is dimensionalized in a protruding shape 54*a*, and thus a reversed primarily scanned image 11*b* may be obtained.

And, a CT image 14 is obtained through CT scanning of the upper and lower jaws (s10).

Here, it may be understood that the inner surface of the denture 50 is an inner surface of the first image matching groove 54 matched with the tooth implanting portion, and the outer surface of the denture 50 is an outer surface of an artificial tooth portion 51 and a gum coupling portion 52. Also, the tooth implanting portion may be a portion at which a natural tooth is lost from the upper or lower jaw and thus the dental implant is performed.

And it may be understood that the denture 50 is an artificially manufactured substitute for a tooth or teeth which is installed at the tooth implanting portion, from which the natural tooth is lost, to chew food. At this time, the denture 50 is provided to include the artificial tooth portion 51 replacing the natural tooth and the gum coupling portion 52 having the first image matching groove 54 matched with an outer surface of the tooth implanting portion.

Specifically, the artificial tooth portion 51 is processed in consideration of the vertical dimension and a shape of a masticating surface so that the masticating surface of an opposing tooth t which faces the artificial tooth portion 51 to be selectively occluded therewith stably meshes with the masticating surface of the artificial tooth portion 51. Therefore, when the patient masticates the food after the denture is installed, patient discomfort may be minimized.

The gum coupling portion 52 extends to substantially cover to a side surface of a gum of the tooth implanting portion. In the case of the upper jaw, the gum coupling portion 52 may be formed to cover a roof of a patient's mouth. At this time, an exterior of the gum coupling portion 52 is manufactured similarly to a shape of a patient's gum to provide aesthetic sensibility. Also, the first image matching groove 54 is formed to have an inner surface profile which is substantially matched with an outer surface profile of the tooth implanting portion.

Consequently, when the patient masticates the food after the denture 50 is installed, movement of the denture 50 is minimized, and the patient discomfort is reduced, and thus patient satisfaction may be considerably improved.

The primarily scanned image including information of the first image matching groove 54 corresponding to the vertical dimension, a shape of the masticating surface and the tooth implanting portion of the patient is obtained through the scanning of such manufactured denture 50. Here, a height and a shape of the crown may be rapidly and easily calculated later through information of the denture 50 obtained from the primarily scanned image.

Meanwhile, when the inner and outer surfaces of the denture 50 are scanned, a plurality of reference markers 40 may be attached to an outside of the denture 50. Herein, the reference markers 40 may be used later as the matching reference points for main matching between the integrated scanned image 13 and the CT image 14.

Specifically, the reference markers 40 may be provided at a plurality of places, preferably, three places or more of the outside of the denture 50. That is, as the reference markers 40 are provided at the plurality of places, matching references between the images are increased in a future image matching process, and thus an image matching degree may be remarkably improved. Therefore, since accuracy and reliability of the surgical guide and the implantation material are enhanced, the patient satisfaction may be considerably improved.

Here, each of the reference markers 40 may be provided to have a shape having a predetermined volume such as a cylinder or a polyprism. At this time, one of upper and lower surfaces thereof opposing to each other may be attached to the outside of the denture 50, and the other one may be used as a matching reference surface in a main matching process.

Meanwhile, since the reference markers 40 are attached to the outside of the denture 50, reliability of an image of the reference markers 40 used as the matching reference points, when the images are matched with each other, may be enhanced.

Specifically, in the case of an edentulous patient, movability of the gum of the tooth implanting portion is high. Therefore, when the reference markers 40 are attached to the tooth implanting portion, the reference markers 40 may be moved, and thus may not be indicated at the same positions of each image.

To solve the problem, the reference markers 40 may be attached to the outside of the denture 50 which is substantially rigid, and thus may prevent the reference markers 40 from being moved. Therefore, positions of the reference markers 40 indicated in each image substantially coincide with each other, and thus when the images are matched with each other, an overlapping degree and the image matching degree may be considerably improved.

Further, the reference markers 40 may be attached to an outer surface of the gum coupling portion 52 to be indicated on each obtained image, and not to obstruct a design of the crown when the crown c is designed through a future three-dimensional occlusion guide image 15. Also, the reference markers 40 may be attached to the denture 50 using a soft resin, an implant adhesive or the like, and may be easily removed after a necessary image is obtained.

Meanwhile, while the denture 50 at which the reference markers 40 are attached is installed at the tooth implanting portion, the secondarily scanned image 12 is obtained through the oral scanning of the patient's upper and lower jaws.

Here, the secondarily scanned image 12 includes an occlusal scanned image obtained through the oral scanning white the patient's upper and lower jaws in which the denture 50 is installed are occluded, and also includes a spaced scanned image obtained through the oral scanning of an exterior of the opposing tooth while the upper and lower jaws are spaced from each other.

Here, the occluded state of the upper and lower jaws means that teeth of the upper and lower jaws are in contact with each other, when a patient's mouth is closed. In the present invention, it may be understood that the occluded state is a state in which the artificial tooth portion 51 of the denture 50 is in contact with the opposing tooth t. And the spaced state may be a state in which the patient's mouth is opened, and the upper and lower jaws are vertically spaced a predetermined distance from each other.

Specifically, the occlusal scanned image includes three-dimensional exterior information in a state in which the artificial tooth portion 51 of the denture 50 is substantially in contact with the opposing tooth t while the upper and lower jaws are occluded. Here, it may be understood that the three-dimensional exterior information in the contact state is shapes of the gum of the opposing tooth t and the gum coupling portion 52 of the denture 50, while the artificial tooth portion 51 and the opposing tooth t are occluded.

And the spaced scanned image includes three-dimensional exterior information of the opposing tooth t in the state in which the upper and lower jaws are spaced from each other. Here, it may be understood that the three-dimensional exterior information of the opposing tooth t is shapes of the opposing tooth t, the gum thereof and the masticating surface of each tooth, and an arrangement relationship.

Meanwhile, the primarily scanned image and the secondarily scanned image 12 are preliminarily matched with each other. Specifically, the secondarily scanned image 12 includes the occlusal scanned image and the spaced scanned image. The primarily scanned image and the secondarily scanned image 12 are automatically overlapped with each other through a computer-based image processing process using a common area between the two images as the reference point. At this time, the common area may be a portion of the opposing tooth t, or, if necessary, a separate overlapping reference point may be set and used.

That is, the secondarily scanned image 12 simultaneously includes the three-dimensional exterior information of the opposing tooth t of the spaced scanned image, and the three-dimensional exterior information of the occlusal scanned image in which the artificial tooth portion 51 and the opposing tooth t are occluded.

As described above, the primarily scanned image and the secondarily scanned image 12 are automatically preliminarily matched with each other, and the first image matching groove 54 is reversed to dimensionalize the image of the first image matching groove 54 from primarily scanned image. Consequently, the integrated scanned image 13 considering the vertical dimension may be obtained.

Specifically, the secondarily scanned image 12 includes the three-dimensional exterior information of each of the occlusal scanned image and the spaced scanned image, and is overlapped and imaged using a predetermined matching reference point, and then indicated on an imaging device. Here, it may be understood that the matching reference point is a common portion between the occlusal scanned image and the spaced scanned image. For example, a certain point of the denture 50 or the reference marker 40 may be the common portion between the images of the opposing tooth t.

And when each scanned image 12 is overlapped through the computer-based imaging device, the images may be automatically matched with each other based on mutually common portions between the exterior information of the denture 50 and the exterior information of the upper and lower jaws including the opposing tooth t. Of course, if necessary, each image may be manually matched by an operator. In this case, an operation for increasing the overlapping degree between the common portions may be performed, and then the preliminarily matching may be performed.

And the first image matching groove 54 is reversed so that the concave image of the first image matching groove 54 included in the primarily scanned image is convexly dimensionalized on the above-described overlapped image. Consequently, the first image matching groove is dimensionalized in a protruding shape 54a, and thus a reversed primarily scanned image 11b may be obtained.

At this time, the inner surface profile of the first image matching groove 54 substantially corresponds to the outer surface of the tooth implanting portion. Therefore, the exterior information of the tooth implanting portion may be easily obtained through only the scanning of the denture 50. Further, a clearer and more accurate image may be obtained by scanning the denture 50 formed of a substantially sold material, rather than directly oral-scanning the outer surface of the tooth implanting portion having the high movability.

Specifically, referring to FIG. 4, an unnecessary image, except an image of the inner surface profile of the first image matching groove 54 and an image of the reference marker 40, is removed from the primarily scanned image. Here, it may be understood that the removed unnecessary image is outer shapes of the artificial tooth portion 51 and the gum coupling portion 52 of the denture 50.

The image of the inner surface profile of the first image matching groove 54 which is formed to be substantially concave is reversed in an image 11a, in which the outer shape of the artificial tooth portion 51 and the gum coupling portion 52 are removed, to be dimensionalized and imagined in the protruding shape 54a. Here, the protruding shape 54a of the first image matching groove substantially corresponds to the outer surface profile of the tooth implanting portion. Therefore, the outer surface profile of the tooth implanting portion may be obtained with only the image obtained through the scanning of the denture 50, rather than the separate oral scanning of the tooth implanting portion.

That is, an image corresponding to the tooth implanting portion may be obtained with only the image obtained by attaching the reference marker 40 to the rigid outer surface of the denture 50, instead of the tooth implanting portion having the high movability.

Therefore, since a process and time for manufacturing a separate impression model of the tooth implanting portion is omitted, a period of time for the dental implant may be remarkably reduced, and a cost for manufacturing the impression model may also be reduced, and thus it is economical.

At this time since the outer shape of the gum coupling portion 52 having a predetermined thickness in the image is removed, a gap may be formed between an image outer surface of the protruding shape 54a of the first image matching groove 54 and an image end of the reference marker 40. To solve this problem, an image of one end of the reference marker 40, a portion of the reference marker 40 attached to the gum coupling portion 52 may extend. And a correction operation which connects the extending image portion with the image outer surface of the protruding shape 54a of the first image matching groove 54 reversed to be dimensionalized may be further performed. Therefore, reliability of information obtained when the integrated scanned image 13 and the CT image 14 are matched with each other may be considerably enhanced.

Of course, if necessary, a reversing process in which the first image matching groove 54 is reversed to be dimensionalized from the primarily scanned image may be first performed, and then an overlapping process with the secondarily scanned image 12 may be performed. Such a modified example belongs to the range of the present invention.

Meanwhile, the occlusal scanned image may be removed from an image in which the secondarily scanned image 12 is overlapped with the primarily scanned image 11b in which the first image matching groove 54 is reversed to be dimensionalized in the protruding shape 54a. Consequently, a vertical dimension value which is intended to be obtained may be easily obtained from the integrated scanned image 13 in which the primarily scanned image 11b and the spaced scanned image are aligned with each other.

A length L from an end of the tooth implanting portion to an end of the opposing tooth t may be calculated in consideration of a height of the opposing tooth t, the vertical dimension value calculated from the integrated scanned image 13 obtained as described above, or the like. And a height of the crown c which will be designed later may be determined using the calculated length L. Meanwhile, it may be understood that the end of the tooth implanting portion is an uppermost end of an alveolus.

That is, since the denture 50 is already manufactured in consideration of the vertical dimension to allow the patient to stably perform a masticating motion, the vertical dimension value may be easily calculated from the integrated scanned image 13.

At this time, a separate process of manufacturing the impression model may be omitted by using the denture 50 which is already being used. Further, the denture 50 is already manufactured in consideration of the inner surface profile, the vertical dimension, a shape of the masticating surface and a tooth arrangement relationship of the first image matching groove 54 corresponding to the tooth implanting portion. Therefore, when the surgical guide 60 and the crown c are manufactured, necessary information may be easily received through only the scanning of the inner surface and the outer surface of the denture 50. Of course, when there is not the denture which is being used by the patient, a provisional denture may be manufactured, and then the above-described processes may be performed.

Two-dimensional and three-dimensional internal tissue information of the patient's mouth may be obtained from the CT image 14 through the CT scanning of the upper and lower jaws. At this time, the two-dimensional and three-dimensional internal tissue information includes a shape and a bone density of an alveolar bone in the patient's mouth obtained through the CT scanning, and may include the image of the reference marker 40. To this end, the reference marker 40 may be formed of a radiopaque material to be indicated on an image when the CT scanning is performed.

Meanwhile, the integrated scanned image 13 and the CT image 14 are overlapped with each other based on the reference marker 40, and matched with each other through the main matching process in a difference map from which the image matching degree between the images is output, and thus the three-dimensional occlusion guide image 15 is obtained (s20).

Specifically, the integrated scanned image 13 may be obtained by preliminarily matching the primarily scanned image with the secondarily scanned image 12 and then reversing the first image matching groove 54 to be dimensionalized from the primarily scanned image.

And the three-dimensional occlusion guide image 15 is obtained through the main matching process using the reference marker 40 indicated in pairs at mutually opposing positions of the integrated scanned image 13 and the CT image 14 as the matching reference.

Specifically, the reference markers 40 included in the integrated scanned image 13 and the CT image 14 are overlapped with each other, and common portions between the integrated scanned image 13 and the CT image 14 are set as comparative areas. And the main matching process is carried out by performing an image correction process in which the images are corrected so that uppermost portions and outermost portions of the comparative areas of the integrated scanned image 13 and the CT image 14 coincide with each other.

Here, each of the integrated scanned image 13 including the exterior information of the opposing tooth t and the denture 50 and the CT image 14 including the internal tissue information of the upper and lower jaws may be converted to three-dimensional vector data and then may be indicated. And the operator may indicate and input a position similar to each pair of reference markers 40 indicated in the integrated scanned image 13 and the CT image 14 as the matching reference point.

At this time, it may be understood that the reference marker indicated in the integrated scanned image 13 is image information obtained from the primarily scanned image, and the reference marker indicated in the CT image 14 is image information obtained through the CT scanning.

Specifically, the pairs of reference markers 40 are matched at mutually corresponding positions of the images, and the images of each pair of reference markers 40 may be overlapped with each other, and thus an initial difference map having a small error may be obtained. The image correction process may be performed in the image matching process through the difference map, and thus the highly accurately image matched three-dimensional occlusion guide image 15 may be obtained.

Here, the image matching degree means that a degree of similarity of the integrated scanned image 13 and the CT image 14 is indicated with an image matching error between the two images. At this time, the image matching degree is varied in proportion to an absolute value of the image matching error. When the image matching error is 0, it may be interpreted that the image matching degree is the highest. That is, as the image matching degree between the reference markers 40 indicated in the images is increased, it may also be interpreted that the image matching degree between mutually opposed portions of the integrated scanned image 13 and the CT image 14 becomes higher.

For example, when the integrated scanned image 13 and the CT image 14 are overlapped with each other based on the reference markers 40, the image matching degree may be indicated with a degree in which a surface of one image protrudes or is recessed from a surface of the other image.

Further, the image matching degree may be calculated through the three-dimensional vector data of each image. Here, the three-dimensional vector data of each image may be converted to the same coordinate system, and height information of the surface of each image may be indicated with a numerical value through the three-dimensional vector data converted to the same coordinate. By comparing the heights of the surfaces of the mutually overlapped images, it may be determined whether the image matching degree is high or low.

When the surface of one image further protrudes than the surface of the other image, the image matching error has a positive value, and when the surface of one image is further recessed than the surface of the other image, the image matching error has a negative value.

Further, since the image matching degree is analyzed and output by colors, the operator may rapidly and intuitively determine accuracy of an image matching result. Therefore, a calculation process of the image may be rapidly performed, and a follow-up correction process for obtaining the accurate three-dimensional occlusion guide image 15 may be smoothly performed.

Meanwhile, the three-dimensional vector data of each image may be digitalized and stored in a computer storage device, and the image processing process for overlapping each image may be performed based on a computer.

Specifically, in the initial difference map in which the integrated scanned image 13 and the CT image 14 are overlapped, information of the alveolar bone and the bone density thereof included in the CT image 14 is included in one set. In addition, the vertical dimension value and the exterior information of the inside of the mouth included in the integrated scanned image 13 are also included in one set.

Comprehensive information included in each image may be provided by overlapping the integrated scanned image 13 with the CT image 14 using the reference markers 40 as the matching reference points. At this time, when the images are overlapped with each other, the image matching degree is indicated at each pixel of the difference map. An image matching process for increasing the image matching degree indicated at each pixel of the difference map is performed.

Here, the uppermost portions and the outermost portions of the comparative areas may coincide with each other using the reference markers 40 indicated in each images as the matching reference points. At this time, the comparative areas are set as common portions between the integrated scanned image 13 and the CT image 14. A process in which the comparative areas are set by calculating the common portions of each image may be automatically performed in an image processing device, or, if necessary, may be manually performed by the operator.

Here, as the common portions of each image are set as the comparative areas, the necessary information may be integrated from each image, and thus an accurate image matching result may be obtained.

Specifically, the integrated scanned image 13 is obtained by overlapping and combining image information continuously scanned by a scanner moving along the inside of the patient's mouth or the outside of the denture 50. At this time, a curvature of the tooth arrangement or the like may be indicated in a distorted state from actual periodontal tissues. The accurate image may be obtained by correcting the distortion with an accurate curvature of the tooth arrangement included in the CT image 14.

When the image matching is completed, a layer in which the image matching degree is indicated may be removed, and thus the three-dimensional occlusion guide image 15 including the integrated scanned image 13 and the CT image 14 may be obtained.

Like this, since the accurate reference points for the image matching are provided through the reference markers 40 installed at the outside of the denture 50, a more accurate image matching result corresponding to various inner states of the patient's mouth may be obtained.

Further, the three-dimensional occlusion guide image 15 may be obtained using the vector data of the integrated scanned image 13 and the CT image 14. That is, the image processing process such as a rotation, an enlargement/reduction and a partial angle correction of each image may be performed by processing the vector data using a computer-based simulation program. Consequently, the image matching degree of the common portions of each image in the difference map may be further enhanced.

Meanwhile, the height of the crown c is set based on the three-dimensional occlusion guide image 15. At this time, the surgical guide 60 including a fixing groove matched with the internal shape of the patient's mouth and a guide hole 61 formed along a fixture implanting position corresponding to the set crown c (s30), Specifically, the three-dimensional occlusion guide image 15 includes the integrated scanned image 13 obtained by preliminary matching the primarily scanned image with the secondarily scanned image 12. At this time, the information includes the exterior information, such as the vertical dimension, the shape of the masticating surface and the gum, provided through the image obtained by scanning the inside of the mouth and the denture 50. Also, the three-dimensional occlusion guide image 15 includes the internal tissue information, such as the bone shape and the bone density, provided through the CT image 14 obtained through the CT scanning. The height of the crown c corresponding to the vertical dimension is calculated based on the three-dimensional occlusion guide image 15 including the above-described information, and thus the crown c may be designed.

At this time, the height and the shape of the crown c, except a shape of the implantation material such as the abutment and the fixture, may be three-dimensionally obtained from the three-dimensional occlusion guide image 15 in which the information included in the integrated scanned image 13 and the CT image 14 is integrated.

Of course, if necessary, the height and the shape of the crown c may be calculated from the integrated scanned image 13. Specifically, the integrated scanned image 13 includes the exterior information of the length L between the end of the tooth implanting portion and the end of the opposing tooth t, and the masticating surface of the opposing tooth t. Therefore, the height of the crown c and the shape of the masticating surface may be easily obtained.

Further, the implanting position of the implantation material may be set by indicating an arrangement state and a position of the artificial tooth portion 51 before the occlusal scanned image is removed from the integrated scanned image 13.

That is, an occlusal height suitable for the patient may be calculated in the image matching process which is gradationally performed before the surgical guide 60 is manufactured, and the accurate crown may be manufactured based on the calculated occlusal height. Therefore, a re-designing and re-installing process due to the inaccurately manufactured crown may be minimized, and the time and cost for the dental implant may be prevented from being wasted, and the dental implant may be rapidly performed.

Further, the surgical guide 60 which accurately guides an installation of the implantation material may be manufactured at the same time when the crown which maximally satisfies the patient is designed and manufactured by obtaining the three-dimensional occlusion guide image 15. Therefore, a foundation technical device for the dental implant which completes the implanting of the fixture and the installing of the abutment and the crown within a short period of time at one procedure may be provided.

Here, the surgical guide 60 includes the fixing groove which is matched with the inside of the patient's mouth, preferably, the tooth implanting portion. And the guide hole 61 is formed along the implanting position of the fixture.

Specifically, the surgical guide 60 is matched with and fixed to the edentulous tooth implanting portion of the upper and lower jaws in the patient's mouth. And while the surgical guide 60 is fixed, a hole for implanting the fixture may be drilled through the guide hole 61.

At this time, a movement of the surgical guide 60 should be minimized so that the fixture is accurately implanted at a predetermined position. To this end, the outer surface of the tooth implanting portion should be matched with and fixed to the fixing groove.

Here, a shape of the fixing groove may be obtained from the protruding shape 54a obtained by reversing the first image matching groove to be dimensionalized in the primarily scanned image, and thus may correspond to the outer surface profile of the tooth. Therefore, since the shape of the fixing groove is matched with the exterior of the tooth implanting portion, the surgical guide 60 may be designed to be stably fixed to the tooth implanting portion.

When the fixing groove is designed, the fixing groove is manufactured so that a direction of the guide hole 61 is set to correspond to an implanting direction of the fixture based on a state in which the surgical guide 60 is fixed to the tooth implanting portion.

Further, the shape and the arrangement state of the crown c may be set based on the three-dimensional occlusion guide image 15 including exterior information of the artificial tooth portion 51 of the denture 50 obtained from the primarily scanned image.

Specifically, the primarily scanned image includes information of the denture manufactured already in consideration of the vertical dimension, the shape of the masticating surface and the arrangement state between teeth to minimize the patient discomfort after the denture is installed at the patient's tooth implanting portion. Therefore, the image matching may be performed so that the exterior information of the artificial tooth portion 51 indicated in the primarily scanned image obtained through the scanning of the denture is further included in the three-dimensional occlusion guide image 15. Therefore, not only the surgical guide 60 for setting the implanting direction and position of the fixture but also the shape and the arrangement state of the crown may be easily calculated from the exterior information of the artificial tooth portion 51.

That is, since overall information for the dental implant may be provided from the primarily scanned image obtained through the scanning of the denture 50 which is being used by the patient, a time for procedure preparation and the procedure may be considerably reduced. Also, since a time for obtaining the image information of the inside of the mouth is shortened, inconvenience of the operator and the patient may be remarkably reduced. Further, since the denture 50 was already manufactured in consideration of the vertical dimension and the shape of the masticating surface to allow the patient to use it without discomfort, reliability of the information provided from the image obtained through the scanning of the denture may be considerably improved.

Meanwhile, the denture 50 of which the inner surface is coated with a curable resin may be installed at the tooth implanting portion, and thus the first image matching groove 54 may be corrected to have a profile formed at the curable resin corresponding to the tooth implanting portion.

Specifically, a gap may be formed between the outer surface of the tooth implanting portion and the inner surface of the first image matching groove 54 of the denture 50. At this time, the curable resin coated on the inner surface of the first image matching groove 54 is hardened while compensating for the gap. Consequently, the first image matching groove 54 may be corrected to be substantially matched with the outer surface profile of the tooth implanting portion.

Since accuracy of the image obtained through the scanning of the corrected denture 50 may be enhanced, the reliability of the surgical guide 60 manufactured when the dental implant is performed may also remarkably improved.

Figure 9:
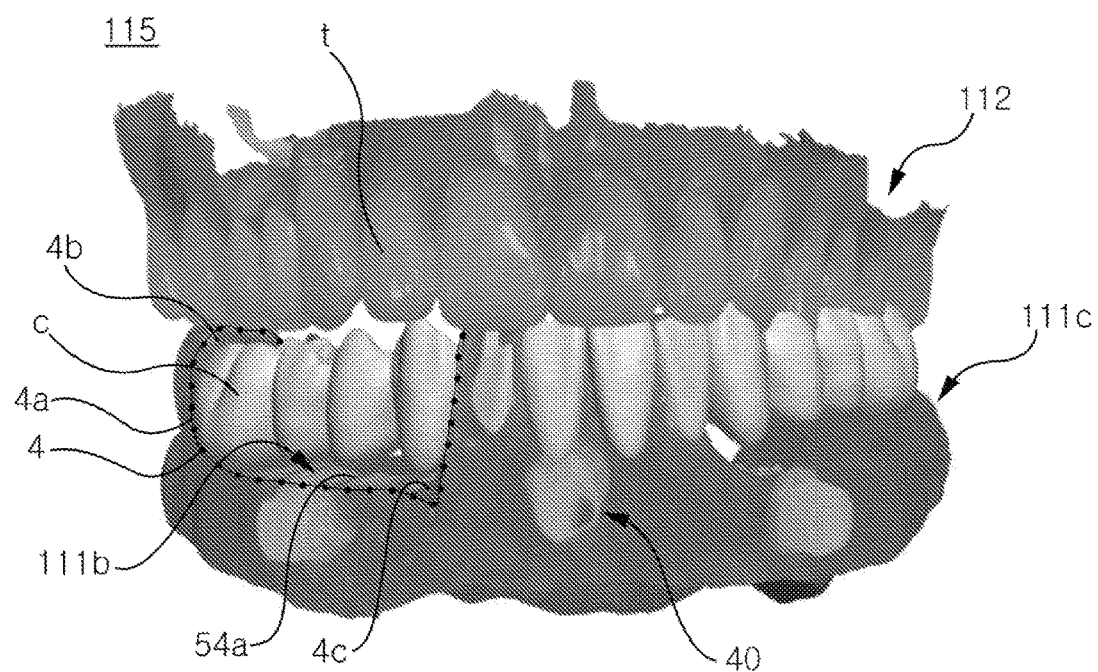
FIG. 9 is an exemplary view illustrating a modified example of the three-dimensional occlusion guide image according to the first embodiment of the present invention.
Figure 10:
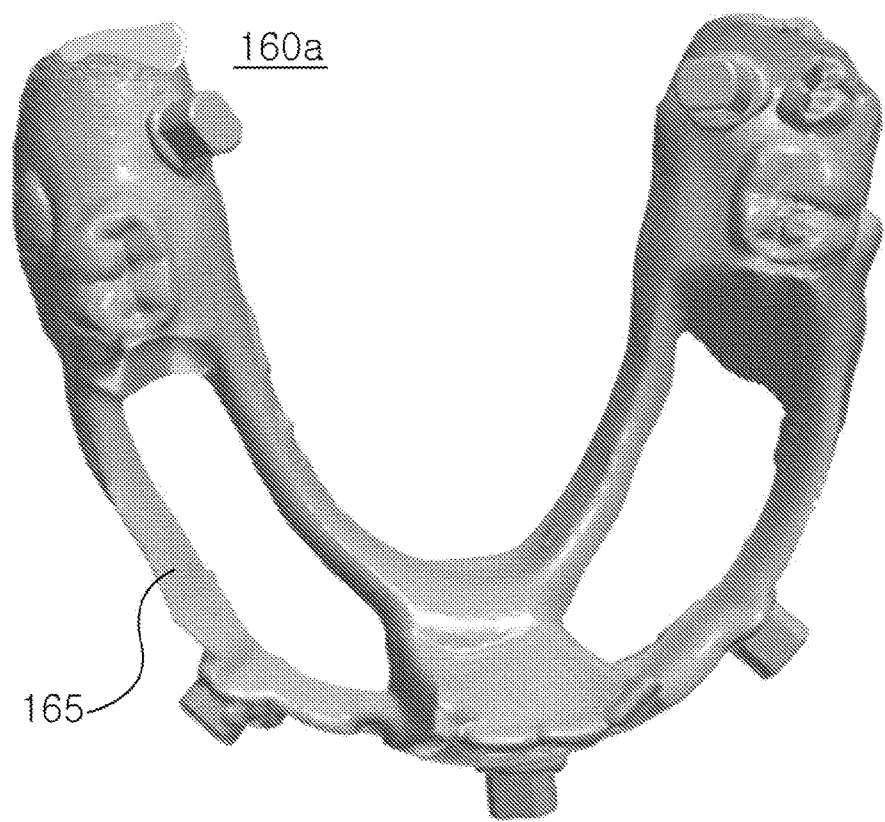
FIG. 10 is an exemplary view illustrating a modified example of the surgical guide for dental implant according to the first embodiment of the present invention.
Figure 11:
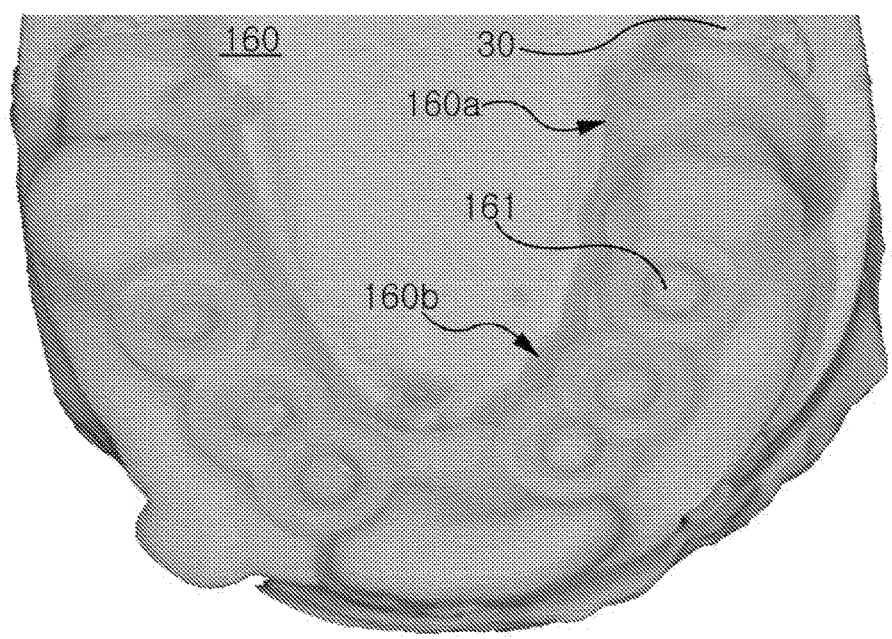
FIG. 11 is an exemplary view illustrating a state in which the modified example of the surgical guide for dental implant according to the first embodiment of the present invention is installed.

Meanwhile, FIG. 9 is an exemplary view illustrating a modified example of the three-dimensional occlusion guide image according to the first embodiment of the present invention, FIG. 10 is an exemplary view illustrating a modified example of the surgical guide for dental implant according to the first embodiment of the present invention, and FIG. 11 is an exemplary view illustrating a state in which the modified example of the surgical guide for dental implant according to the first embodiment of the present invention is installed. In the modified example, since a basic structure of the surgical guide, except the designing and manufacturing process thereof, is the same as that of the first embodiment, detailed description thereof will be omitted.

As illustrated in FIGS. 9 to 11, the protruding shape 54a of the first image matching groove image which is reversed to be dimensionalized, a secondarily scanned image 112 corresponding to the opposing tooth t, and the CT image are overlapped and indicated in a three-dimensional occlusion guide image 115. At this tithe, an imitation guide image 111c may be virtually arranged at an outside of the protruding shape 54a of the first image matching groove image.

Here, the irritation guide image 111c may be obtained through the following process. First, an artificial tooth boundary area of the denture is selected and input corresponding to the implanting position of the implantation material in the primarily scanned image. At this time, it may be understood that the implanting position of the implantation material is a region of the tooth implanting portion in which the implanting of the implantation material is substantially planned.

Also, it may be understood that the artificial tooth boundary area of the denture is an outer boundary portion of the artificial tooth portion corresponding to the implanting position of the implantation material. For example, when it is assumed that the implanting position of the implantation material corresponds to $36^{th}$ and $37^{th}$ teeth of the lower jaw, the artificial tooth boundary area of the denture may be between the artificial teeth corresponding to the $36^{th}$ tooth and $35^{th}$ tooth adjacent thereto and between the artificial teeth corresponding to the $37^{th}$ tooth and $38^{th}$ tooth adjacent thereto.

Specifically, an implanting area portion is set by selecting and inputting a plurality of boundary points 4 along a boundary line between an artificial tooth of the denture corresponding to the implanting position of the implantation material and a peripheral artificial tooth portion adjacent to the artificial tooth of the denture corresponding to the implanting position of the implantation material. Of course, the boundary line may be a boundary between the artificial teeth, or may be a boundary between the artificial tooth portion and the gum coupling portion.

At this time, closed surfaces 4c and 4d located at an inside of a connection line 4a which connects each boundary point 4 with another adjacent boundary point 4 are calculated, and an inside of each closed surface 4c or 4d may be set as the implanting area portion. When the set implanting area portion is removed, the imitation guide image 111c may be obtained. At this time, a part of the primarily scanned image 111b in which the first image matching groove image is reversed to be dimensionalized in the protruding shape 54a may be exposed through a portion in which the implanting area portion is removed.

Meanwhile, the height of the crown c is set based on the three-dimensional occlusion guide image 115, and a surgical guide 160 is designed and three-dimensionally printed based on the three-dimensional occlusion guide image 115 and the imitation guide image 111c. Here, the surgical guide 160 may be manufactured as a double guide including a first guide 160a and a second guide 160b. At this time, in the modified example, a method for setting the height of the crown, and designing and manufacturing the crown is the same as that of the first embodiment, detailed description thereof will be omitted.

Specifically, the fixing groove matched with a tooth implanting portion 30 based on the imitation guide image 111c, and an opening 165 corresponding to the removed implanting area portion are formed at the first guide 160a. A guide hole 161 in which the implanting area portion is formed to be dimensionalized and to be connected to the opening 165 is formed along the implanting position of the fixture at the second guide 160b.

At this time, the first guide 160a may be easily manufactured based on the denture which is already manufactured to be substantially matched with the tooth implanting portion 30. Therefore, a match rate between the fixing groove and the tooth implanting portion 30 is enhanced, thus reliability of the dental implant may be remarkably improved.

The second guide 160b having the guide hole 161 is removably disposed at the opening 165 formed by removing the implanting area portion. Here, it is preferable that the guide hole 161 is formed along the implanting position of the fixture. Consequently, by just separating the second guide 160b after the fixture is implanted, the abutment and the crown may be continuously fastened without separating of the first guide 160a.

Further, since a shape of the artificial tooth portion around the opening 165 is three-dimensionally printed, the operator may easily grasp an arrangement relationship with peripheral teeth at the same time when the crown c is coupled to the first guide 160*a*, procedure convenience may be considerably improved.

At this time, an aligning protrusion and an aligning image matching groove which guide an aligning and coupling process may be formed at mutually opposed surfaces of the second guide 160*b* and the opening 165 formed at the first guide 160*a*. Consequently, since the second guide 160*b* may be substantially integrally fixed to the opening 165 of the first guide 160*a*, reliability of the implanting position of the implantation material implanted along the guide hole 161 may be further enhanced.

In addition, an aligning piece may be provided so that the first guide 160*a* to which the second guide 160*b* is coupled is firmly fixed to an outside of the tooth implanting portion 30. Specifically, the aligning piece has a body portion which is filled in a space between the denture and the opposing tooth t to support the space and to guide an occlusal position when the upper and lower jaws at which the denture is installed are occluded. And an image matching portion which is reversed so that end shapes of the opposing tooth and the denture is dimensionalized is formed at an outer surface of the body portion.

At this time, the aligning piece may be manufactured by injecting a curable impression resin between the upper and lower jaws in which the denture 50 is installed. Specifically, the curable impression resin or putty of which a shape before hardened is freely deformable is injected between the opposing tooth and the denture installed at the outside of the tooth implanting portion 30. And when the injected impression resin is hardened, the body portion supporting the space between the denture and the opposing tooth is formed.

Here, the curable impression resin is injected to cover an end of the artificial tooth portion of the denture and an end of the opposing tooth, and thus the image matching portion in which an end image of each tooth is reversed may be formed. At this time, the curable impression resin may be injected to be easily separated from the denture and the opposing tooth, and also to cover each end of the denture and the opposing tooth, such that the ends of the denture and the opposing tooth are caught by the image matching portion, and thus each position thereof is restricted.

The aligning piece manufactured as described above may be used when the first guide 160*a* is installed at the tooth implanting portion 3. Specifically, the first guide 160*a* is installed at the outside of the tooth implanting portion 30, and the aligning piece is disposed between an upper side of the first guide 160*a* and the end of the opposing tooth.

At this time, by just installing the end of the first guide 160*a* and the end of the opposing tooth t at the image matching portion, which is formed at the aligning piece, to be restricted, the first guide 160*a* may be aligned at a preferable position of the tooth implanting portion 30. And a fixing pin of which an end is implanted in the gum may pass through and may be fastened to a side surface of the first guide 160*a*, and thus the first guide 160*a* may be firmly fixed to the tooth implanting portion 30.

That is, since the first guide 160*a* is substantially manufactured based on an exterior of the denture 50, the image matching portion formed at the aligning piece may be correspondingly matched with ends of peripheral tooth shapes formed at the opposing tooth t and the first guide 160*a*.

Therefore, since the first guide 160*a* may be accurately aligned at and firmly fixed to the preferable position according to a dental implant plan using the aligning piece manufactured using the denture, the implantation material may be implanted at an accurate position.

Meanwhile, the shape and the arrangement state of the crown c may be set based on the three-dimensional occlusion guide image 115 including the exterior information of the artificial tooth portion of the denture obtained from the primarily scanned image. And the guide hole 161 of the second guide 160*b* may be set based on the implanting position of the fixture which is set based on the shape and the arrangement state of the crown c.

Specifically, the denture is already manufactured in consideration of the vertical dimension, the shape of the masticating surface, and the arrangement state between the teeth, as described above. Therefore, the three-dimensional occlusion guide image 115 including the primarily scanned image obtained through the scanning of the denture may include information which may calculate the shape and the arrangement state of the crown c. That is, the shape and the implanting position and direction of the crown may be calculated and designed from the exterior information of the artificial tooth portion of the denture and the exterior information of the opposing tooth t.

Also, the implanting direction of the fixture may be calculated according to the implanting position and direction of the crown, and the guide hole 161 may be easily set based on the calculated implanting direction of the fixture.

Consequently, since overall information for the dental implant is provided from the scanned image of the denture, the surgical guide 160 and the implantation material which are conveniently manufactured and have the remarkable improved accuracy may be manufactured. Therefore, the procedure preparation for the dental implant and the time for the procedure may be considerably reduced, and thus the operator and patient discomfort may be remarkably solved.

Figure 12:
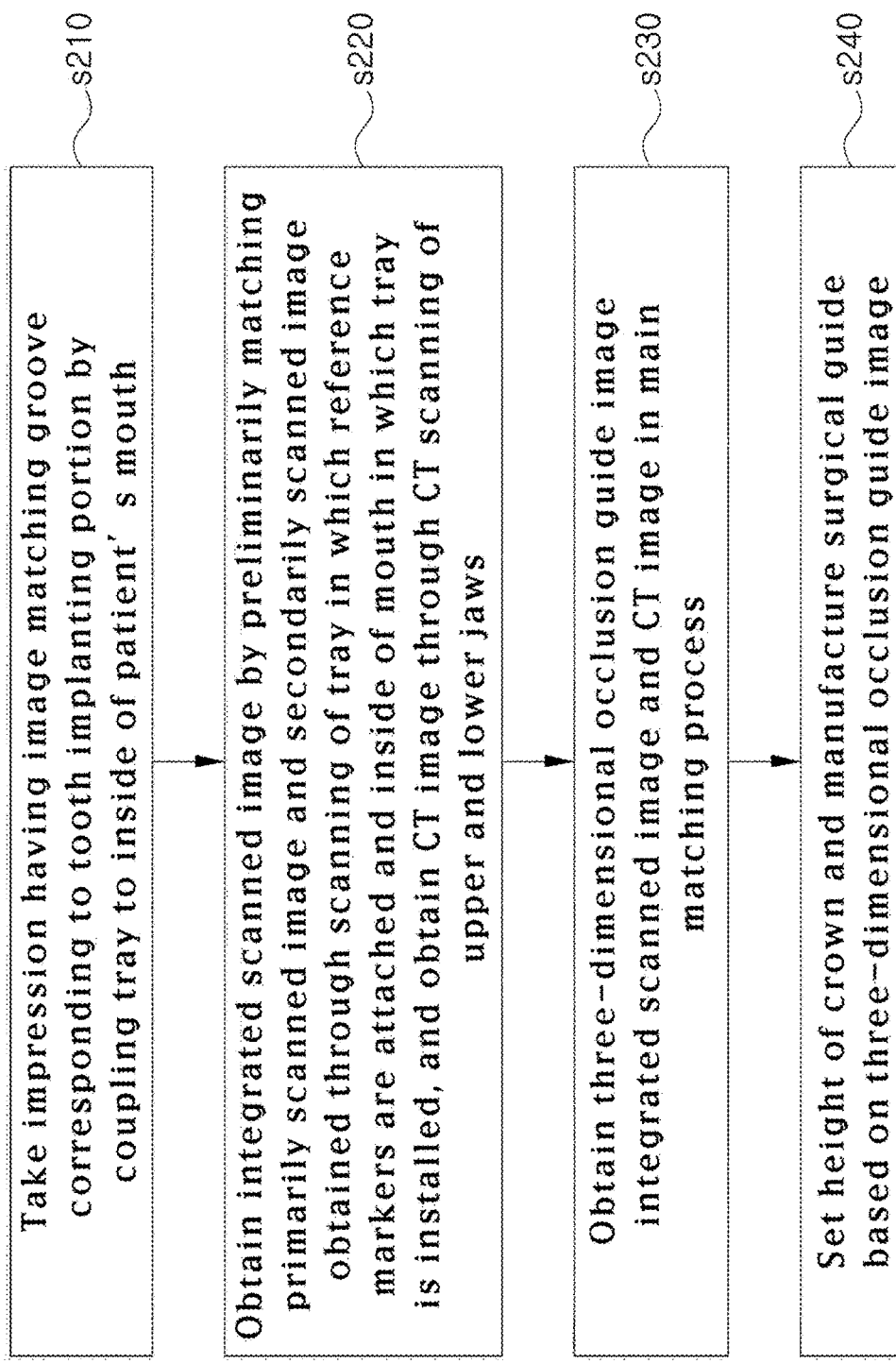
FIG. 12 is a flowchart illustrating a method for manufacturing a surgical guide, and a crown and an abutment in a mouth for a dental implant according to a second embodiment of the present invention.
Figure 13:
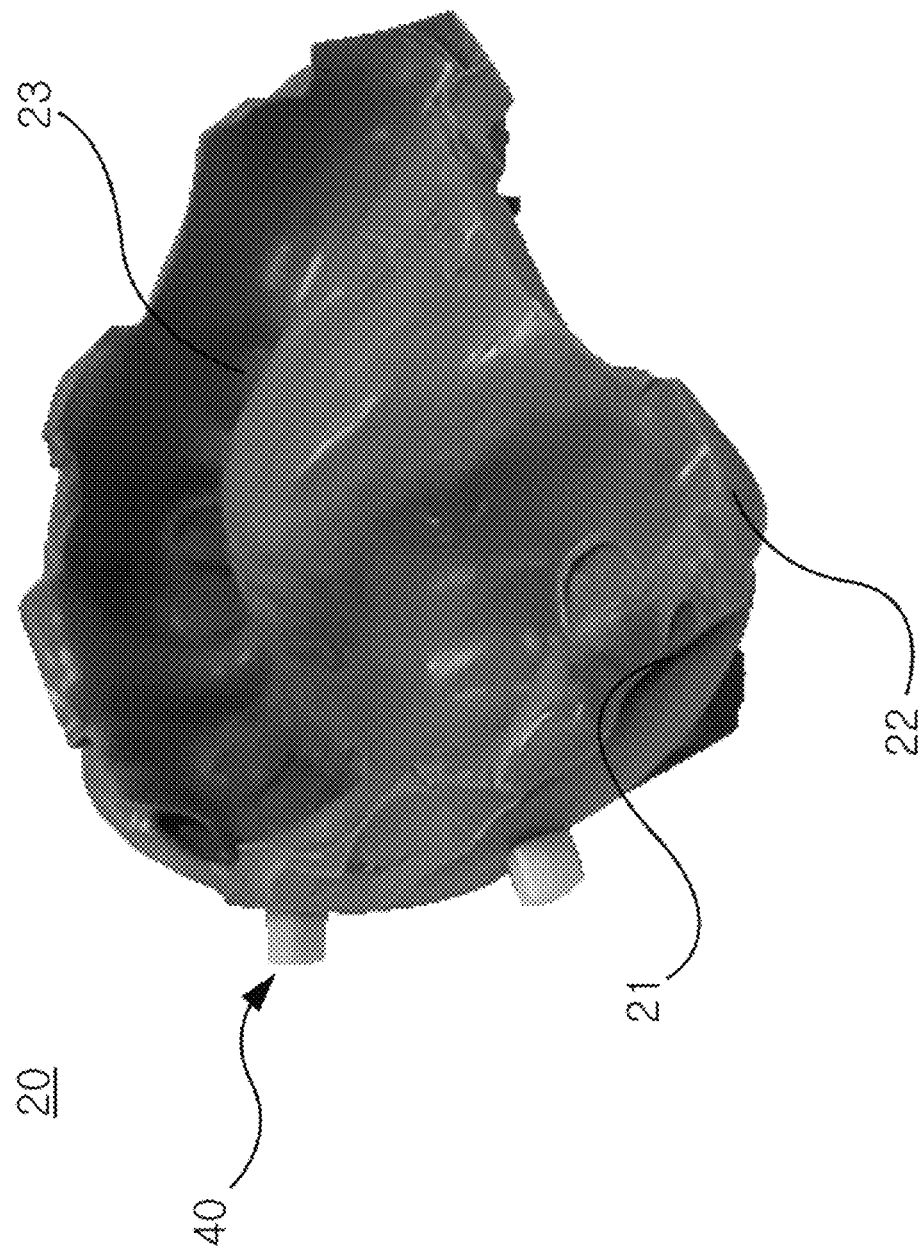
FIG. 13 is an exemplary view illustrating a tray in which an impression is taken according to the second embodiment of the present invention.
Figure 14:
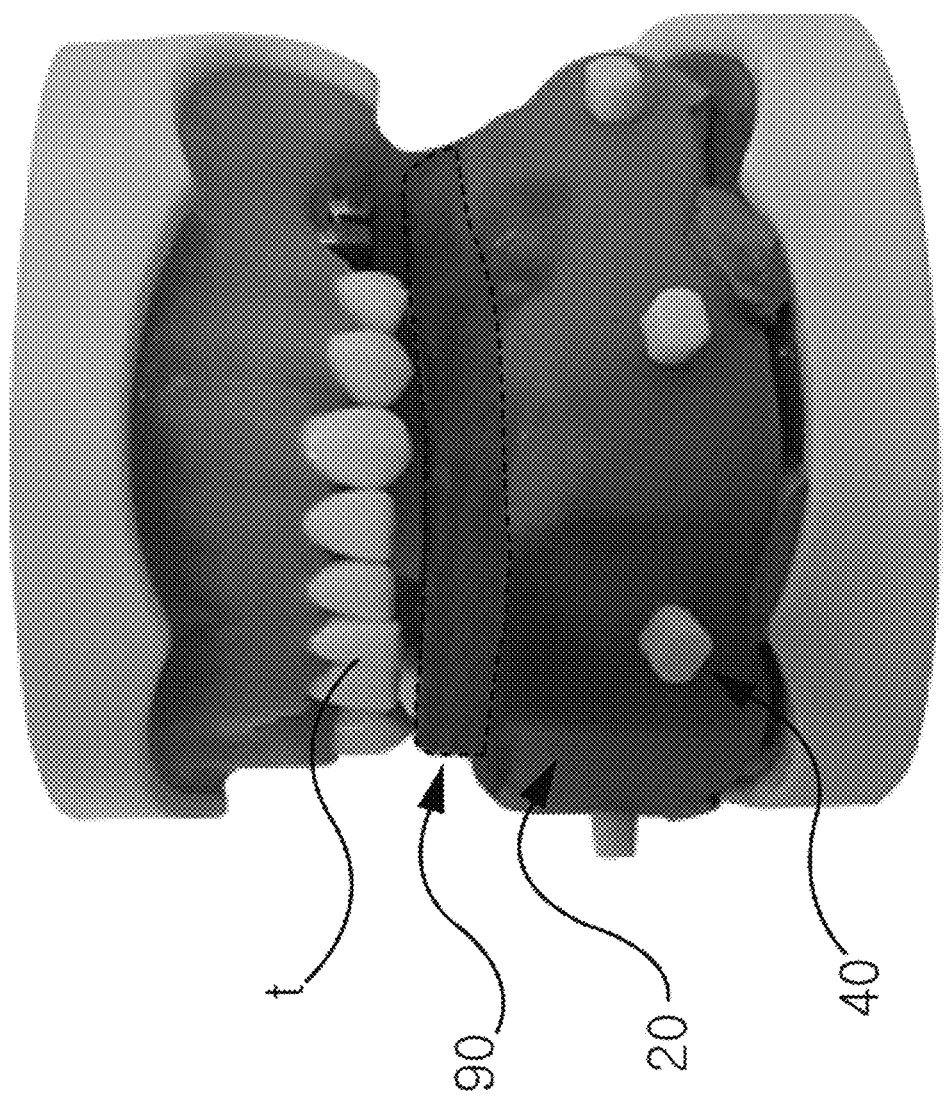
FIG. 14 is an exemplary view illustrating a occluded state of upper and lower jaws while the tray having a predetermined occlusal height is installed according to the second embodiment of the present invention.

FIG. 12 is a flowchart illustrating a method for manufacturing the surgical guide, and the crown and the abutment in the mouth for the dental implant according to a second embodiment of the present invention; FIG. 13 is an exemplary view illustrating a tray in which an impression is taken according to the second embodiment of the present invention; and FIG. 14 is an exemplary view illustrating a occluded state of the upper and lower jaws in which the tray having a predetermined occlusal height is installed according to the second embodiment of the present invention. In the second embodiment, since a basic structure of the surgical guide, except an image obtaining process using the tray, is the same as that of the first embodiment, detailed description thereof will be omitted.

As illustrated in FIGS. 12 to 14, the surgical guide and the implantation material may be manufactured through image information obtained using the tray 20.

Specifically, the tray 20 having the plurality of reference markers 40 attached to a side surface thereof, and a tooth arrangement groove 21 formed at an inner surface thereof to inject an impression material 22 therethrough is coupled to the inside of the patient's mouth. Therefore, the impression material 22 is pressed, and thus an impression in which a second image matching groove 23 corresponding to the shape of the tooth implanting portion is formed is taken (s210).

Here, the tray 20 is formed to have a shape corresponding to the tooth arrangement in the mouth, and located between the upper and lower jaws, while the impression material 22 such as alginate, silicone and rubber is put on a surface thereof opposed to the tooth implanting portion. When a pressure is applied so that the upper and lower jaws are occluded, the impression in which the second image matching groove 23 corresponding to the shape of the tooth implanting portion is engraved at the gel-state impression material 22 may be taken.

At this time, the tooth arrangement groove 21 may be formed along an edge of at least one of upper and lower surfaces of the tray 20 to prevent the impression material 22 from being pushed to an outside by the pressure, when the upper and lower jaws are occluded. Specifically, a side surface of the tooth arrangement groove 21 extends along the edge of the tray 20 to have a predetermined height and thus to accommodate the impression material 22 therein. At this time, the side surface may extend to have the predetermined height which accommodates a sufficient amount of the impression material 22 to clearly take the impression of the tooth implanting portion and also which does not interfere with a peripheral gum region, for example, the roof of the mouth.

That is, since the impression material 22 fills an inside of a bottom surface and the side surface, and is prevented from leaking to an outside, the impression of the inside of the patient's mouth may be more clearly taken. Consequently, since accuracy of an image obtained through the scanning of the tray 20 is enhanced, reliability of the dental implant plan designed through the image may be considerably improved.

Although not shown in the drawings, a handle which is grasped by the operator to move and install the tray 20 at the inside of the patient's mouth may be formed at an outside of the tray 20. Here, the handle may extend from an outer side surface of the tooth arrangement groove 21 not to obstruct the occlusion between the upper and lower jaws.

In addition, the plurality of reference markers 40 may be attached to the outside of the tray 20. Here, since the reference markers 40 has the same structure as that of the first embodiment, detailed description thereof will be omitted.

That is, since the reference markers 40 are attached to the outside of the tray 20 formed of a rigid material, a movement thereof is prevented, and the positions of the reference markers 40 indicated in the images substantially coincide with each other. Therefore, the image matching degree between the images is enhanced, and the accuracy and the reliability of the surgical guide and the implantation material designed from the image may be remarkably improved.

At this time, as long as the reference markers 40 are attached to the outside of the tray 20, attaching positions thereof are not limited. However, the reference markers 40 may be attached to the side surface of the tray 20, except a tooth area of the tooth implanting portion at which the dental implant is performed. At this time, it may be understood that the side surface of the tray 20 is the same as the outer side surface of the tooth arrangement groove 21.

Consequently, when the crown is designed through a three-dimensional occlusion guide image which will be obtained later, designing of the crown may be prevented from being obstructed by an image of the reference markers 40. Here, it may be understood that the tooth area is a portion from which a natural tooth is lost and thus in which the implantation material is substantially implanted, and is also an area corresponding to an uppermost end of the alveolus.

Meanwhile, an occlusal base 90 set to have an occlusal height corresponding to the opposing tooth t is stacked on an outside of the tray 20 in which the impression having the second image matching groove 23 is taken at an inside thereof. A primarily scanned image is obtained through the scanning of outer and inner surfaces of the tray 20 on which the occlusal base 90 is stacked. Also, a secondarily scanned image is obtained through the oral scanning of the upper and lower jaws, while the tray 20 is installed. The primarily scanned image and the secondarily scanned image are preliminarily matched with each other, and the second image matching groove 23 is reversed so that an image of the second image matching groove 23 is dimensionalized from the primarily scanned image, and thus an integrated scanned image considering the vertical dimension is obtained. Also, a CT image is obtained through the CT scanning of the upper and lower jaws (S220). Here, in the embodiment, it may be understood that the occlusion is a state in which an upper surface of the occlusal base 90 stacked on the tray 20 is in contact with an end of the opposing tooth t facing the upper surface.

Specifically, while the tray 20 is installed at the tooth implanting portion, and the upper and lower jaws are occluded, the occlusal base 90 may be stacked to have a thickness corresponding to a space between the opposing tooth t and the outside of the tray 20. At this time, the occlusal base 90 may be formed of a material, such as a wax, of which a shape may be easily deformed by pressing or cutting, and thus the thickness is selectively and easily adjusted according to patient's mastication feeling, while the predetermined shape is maintained.

And while the tray 20 on which the occlusal base 90 is stacked is installed at the tooth implanting portion, the upper and lower jaws are occluded. At this time, the thickness of the occlusal base 90 may be adjusted according to the patient's mastication feeling, and thus the occlusal height suitable for the patient may be set.

At this time, when the upper and lower jaws are occluded while the tray 20 in which the occlusal base 90 is stacked at the outside thereof is installed at the tooth implanting portion, a mastication mark corresponding to the end of the opposing tooth t is formed at the upper surface of the occlusal base 90. And the thickness of the occlusal base 90 is adjusted by repeating the cutting of the upper surface of the occlusal base 90 corresponding to a depth of the mastication mark until the patient feels comfortable, and thus the occlusal height may be set.

Further, the occlusal height is calculated according to the patient's mastication feeling together with operator's diagnosis. Therefore, the occlusal height may be calculated to maximize procedure satisfaction, while does not give a strain on a patient's temporomandibular joint. Here, the mastication feeling may be determined by a patient's direct expression of opinion, and, if necessary, may be determined by measuring an electric or chemical signal of a peripheral portion of the temporomandibular joint or jaw muscle.

Also, the occlusal base 90 may be stacked to a thickness, which is thicker than an expected occlusal height, so as to easily adjust the thickness, and then the cutting of the upper surface is repeatedly performed, and thus the occlusal height suitable for the patient to feel comfortable may be set.

Meanwhile, the outer and inner surfaces of the tray 20 in which the impression having the second image matching groove is taken at the inside thereof, and the occlusal base 90 is adjusted to have the predetermined occlusal height at the outer surface thereof, and the plurality of reference markers 40 are attached to the side surface thereof are scanned. Thus, the primarily scanned image may be obtained.

The tray 20 is installed at the inside of the patient's mouth. At this time, since the tray 20 is installed so that the second image matching groove 23 is matched with the tooth implanting portion, the occlusal base 90 may be disposed to be occluded with the opposing tooth t.

While the tray 20 is installed, the upper and lower jaws are occluded, and the secondarily scanned image is obtained through the oral scanning, and also the CT image is obtained through the CT scanning. At this time, the secondarily scanned image may further include an occlusal scanned image obtained through the scanning in the state in which the upper and lower jaws in which the tray 20 is installed are occluded, and a spaced scanned image obtained through the scanning of an exterior of the opposing tooth while the upper and lower jaws are spaced from each other.

Meanwhile, the secondarily scanned image in which the occlusal scanned image and the spaced scanned image are overlapped is automatically preliminarily matched with the primarily scanned image. At this time, the integrated scanned image is obtained by reversing the second image matching groove 23 so that the image of the second image matching groove 23 formed at the tray 20 is dimensionalized from the primarily scanned image. Here, since an image matching method for obtaining the integrated scanned image is the same as that of the first embodiment, detailed description thereof will be omitted.

A length from the end of the tooth implanting portion to the end of the opposing tooth t may be calculated in consideration of the vertical dimension and the height of the opposing tooth calculated from the integrated scanned image obtained as described above. Specifically, the occlusal base 90 which is adjusted to have the occlusal height suitable for the patient to have comfortable mastication feeling is stacked at the outer surface of the tray 20. And the tray 20 on which the occlusal base 90 is stacked is installed at the inside of the mouth, and thus each scanned image may be obtained. Consequently, the vertical dimension may be easily calculated from the integrated scanned image obtained through the preliminary matching between the scanned images.

At this time, in the embodiment, by just scanning the tray 20 having the second image matching groove 23, the exterior information of the tooth implanting portion may be easily received. That is, in the dental implant, the shape of the tooth implanting portion may be easily obtained using the tray 20, which is used in the process for taking the inside impression of the mouth, to manufacture the denture to be temporarily used for a time required for manufacturing the implantation material, and thus it is economical.

Meanwhile, the integrated scanned image and the CT image are overlapped based on the reference markers, and matched through a main matching process in a difference map from which the image matching degree between the images is output, and thus the three-dimensional occlusion guide image is obtained (s230). Here, since the main matching process between the integrated scanned image and the CT image is the same as that of the first embodiment, detailed description thereof will be omitted.

And the height of the crown c is set based on the three-dimensional occlusion guide image. At this time, the surgical guide including the fixing groove which is matched with the internal shape of the patient's mouth and the guide hole which is formed along the implanting position of the fixture corresponding to the set crown c is manufactured (s240).

At this time, the shape and the arrangement state of the crown c may be set based on the three-dimensional occlusion guide image including information of the arrangement of the opposing tooth t and the masticating surface obtained from the secondarily scanned image. Further, the secondarily scanned image includes the occlusal scanned image obtained through the scanning in a state in which the tray 20 including the occlusal base 90 having the adjusted occlusal height is installed. Therefore, the vertical dimension may be easily calculated through the three-dimensional occlusion guide image. Meanwhile, since a method for designing the crown c and manufacturing the surgical guide based on the three-dimensional occlusion guide image is the same as that of the first embodiment, detailed description thereof will be omitted.

That is, in the embodiment, even in the case of the patient who does not have basic information of the inside of the mouth, the operator may fill the tooth arrangement groove 21 of the tray 20 with the impression material 22, and then may easily and rapidly take the impression to establish the dental implant plan. Also, since the image is obtained together with the taking of the impression by attaching the reference markers 40 to the rigid outer surface of the tray 20, instead of the tooth implanting portion having the high movability, a matching reference position between the obtained images may be clear. Therefore, the reliability of the surgical guide and the implantation material which are designed and manufactured based on the three-dimensional occlusion guide image obtained through the matching of the images may be remarkably enhanced.

Figure 15:
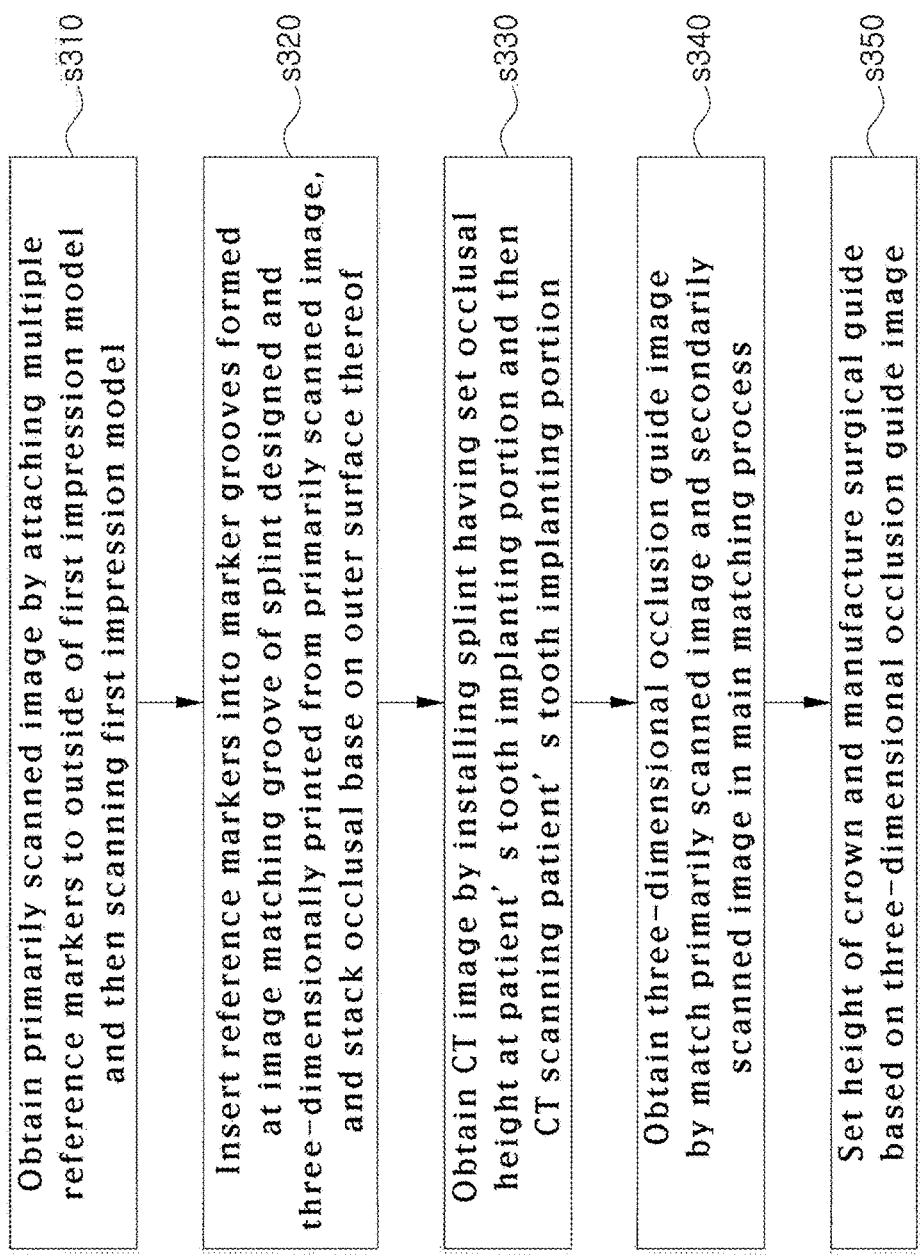
FIG. 15 is a flowchart illustrating a method for manufacturing a surgical guide, and a crown and an abutment in a mouth for a dental implant according to a third embodiment of the present invention.
Figure 16:
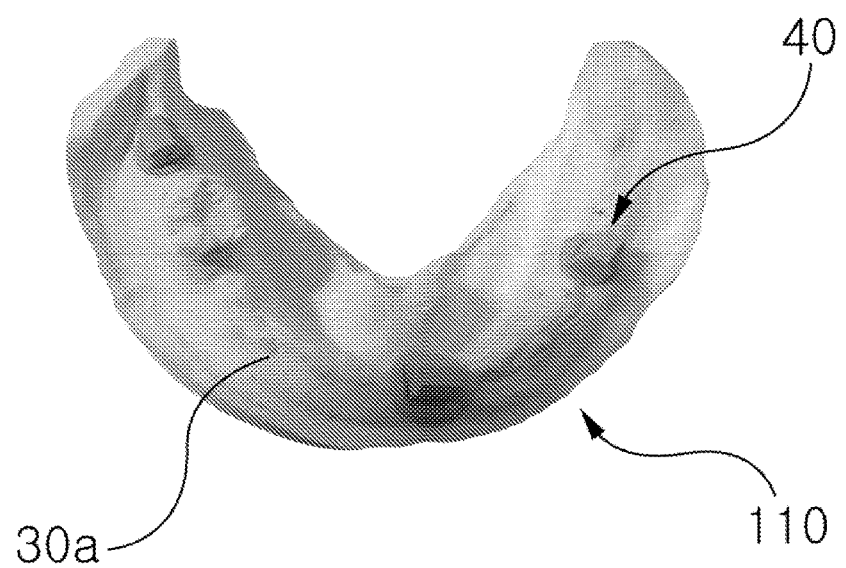
FIG. 16 is an exemplary view illustrating a first impression model to which a reference marker is attached according to the third embodiment of the present invention.
Figure 17:
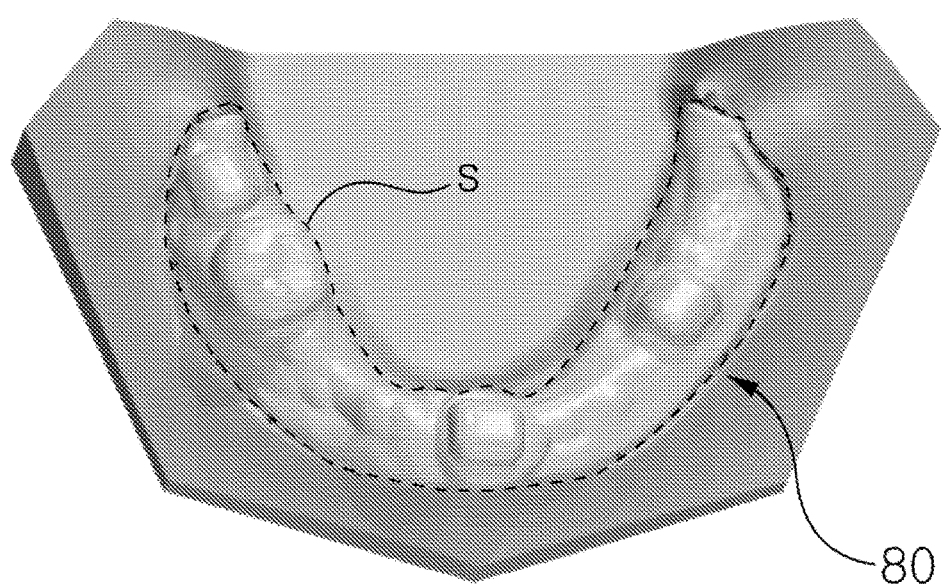
FIG. 17 is an exemplary view illustrating a splint manufacturing process according to the third embodiment of the present invention.
Figure 18:
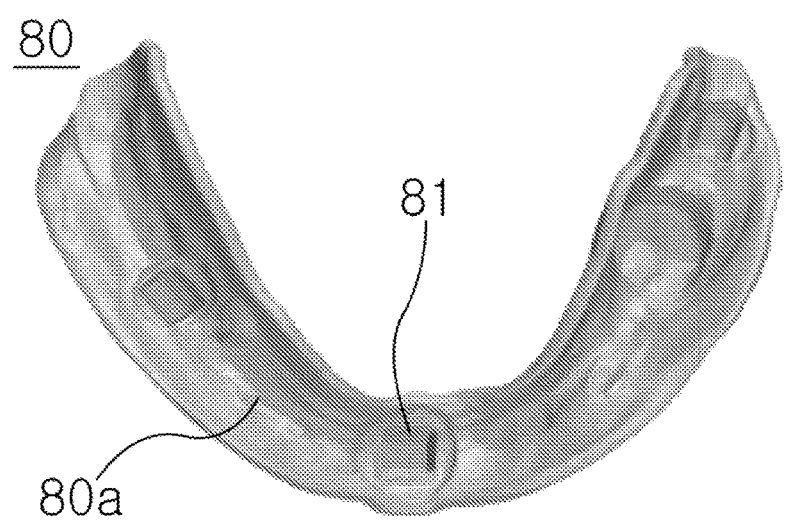
FIG. 18 is an exemplary view illustrating an inner surface of the splint according to the third embodiment of the present invention.
Figure 19:
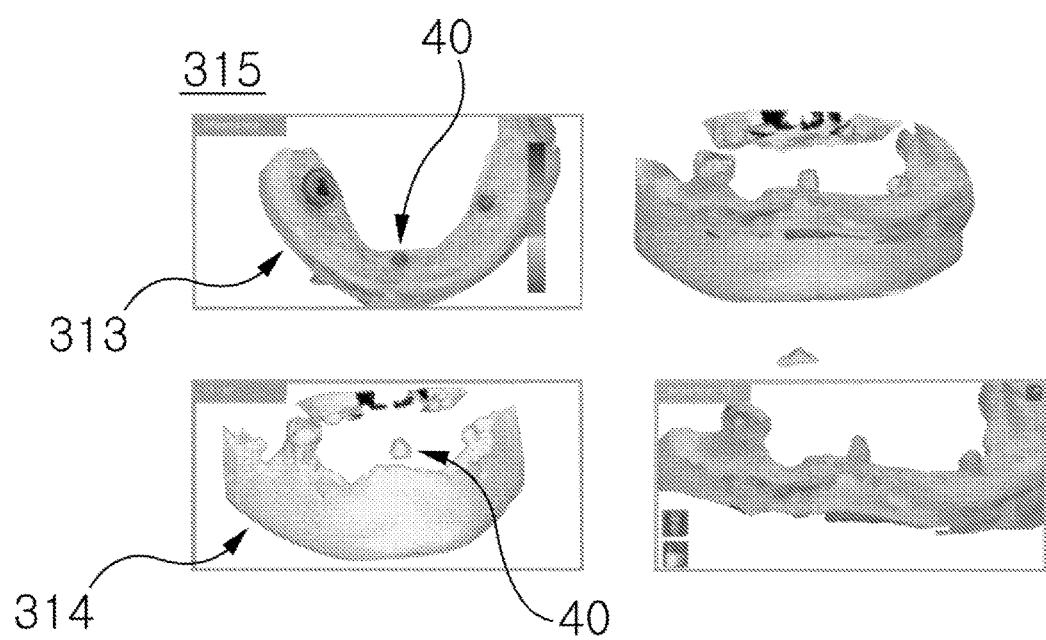
FIG. 19 is an exemplary view illustrating a matching process for obtaining a three-dimensional occlusion guide image according to the third embodiment of the present invention.

Meanwhile, FIG. 15 is a flowchart illustrating a method for manufacturing the surgical guide, and the crown and the abutment in the mouth for the dental implant according to a third embodiment of the present invention, FIG. 16 is an exemplary view illustrating a first impression model to which a reference marker is attached according to the third embodiment of the present invention, FIG. 17 is an exemplary view illustrating a splint manufacturing process according to the third embodiment of the present invention, FIG. 18 is an exemplary view illustrating an inner surface of the splint according to the third embodiment of the present invention, and FIG. 19 is an exemplary view illustrating a matching process for obtaining a three-dimensional occlusion guide image according to the third embodiment of the present invention. In the third embodiment, since a basic structure of the surgical guide, except an image obtaining process using the splint, is the same as that of the first embodiment, detailed description thereof will be omitted.

As illustrated in FIGS. 15 to 19, the surgical guide and the implantation material may be manufactured through image information obtained using the splint 80.

Specifically, the primarily scanned image is obtained through the scanning in a state in which the plurality of reference markers 40 are attached to an outside of the first impression model 110 manufactured corresponding to the patient's tooth implanting portion (s310).

Here, the first impression model is manufactured through the following process. First, the impression in which the shape of the tooth implanting portion is engraved is taken by coating the outer surface of the tooth implanting portion with the impression material such as alginate, silicone and rubber. And the first impression model 110 may be manufactured by filling an inside of the impression with plaster or zinc oxide eugenol ointment for impression and then hardening it. At this time, it may be understood that the inside of the impression is a portion at which the shape of the tooth implanting portion is engraved. Such a method of manufacturing the impression model is a method which is widely used by the operator, for example, in a dental clinic in which the dental implant is performed, and thus the operator may easily manufacture the impression model.

The plurality of reference markers 40 are attached to a plurality of positions of the outside of the first impression model 110. Here, the reference marker 40 is a matching reference for matching the images obtained for the dental implant, and three or more reference markers 40 may be attached.

Of course, if necessary, the reference markers 40 may be directly attached to the inside of the patient's mouth. However, since the gum has the high movability, and thus the reference markers 40 are not fixed substantially, it is preferable that the reference markers 40 be fixed to the outside of the first impression model 110.

Also, as long as the reference markers 40 are attached to the outer surface of the tooth implanting portion, attaching positions thereof are not limited. However, the reference markers 40 may be attached to a tooth area 30*a* of the tooth implanting portion in which the dental implant is substantially performed. When the first impression model 110 to which the reference markers 40 are attached is scanned, a primarily scanned image 311 corresponding to an scanned image of the outer surface of the tooth implanting portion to which the reference markers 40 are attached may be obtained.

At this time, processes in which the reference markers 40 are attached and the primarily scanned image 311 is obtained may be performed, for example, at a manufacturer having dental technician services in which the implantation material and a tool used in the dental implant are manufactured and supplied. Specifically, when the first impression model 110 manufactured by the operator side is transferred to the manufacturer side, the manufacturer side attaches the reference markers 40 to the outside of the first impression model 110.

And the primarily scanned image 311 may be obtained by scanning the outer surface of the first impression model 110 to which the reference markers 40 are attached. At this time, the primarily scanned image 311 may be converted to three-dimensional vector data through the scanning, and the converted information may be digitalized and then stored in a storage device of a computer including a simulation program.

That is, by just transferring the first impression model 110, which is easily manufactured corresponding to the tooth implanting portion, to the manufacturer side, the scanned image may be obtained using scanning equipment provided at the manufacturer side. Therefore, even though the operator side does not have the scanning equipment, or is inexperienced in how to operate the scanning equipment, the accurate scanned image required for the dental implant plan may be obtained. Also, a cost for separately purchasing the scanning equipment may be reduced, and it may solve problems of inconvenience in which the patient should visit the manufacturer side to scan the inside of the mouth.

Of course, if necessary, the operator side having the scanning equipment may attach the reference markers 40 to the outside of the first impression model 110, may perform the scanning, and then may obtain the primarily scanned image 311. And the obtained primarily scanned image 311 may be transmitted to the manufacturer. Such a modified example belongs to the range of the present invention.

In addition, a second impression model corresponding to the opposing tooth may be manufactured together with the first impression model 110. Here, a basic method for manufacturing the second impression model is the same as the method for manufacturing the first impression model 110, and thus detailed description thereof will be omitted.

And the secondarily scanned image may also be obtained through the scanning of the second impression model. Here, the secondarily scanned image includes three-dimensional exterior information including the arrangement shape of the opposing tooth and the shape of the masticating surface. Of course, if necessary, the scanning may be performed in a state in which the reference markers 40 are attached to predetermined positions of the second impression model. However, in the case of the opposing tooth, a rigid outer surface of a tooth may be designated as a fixed comparative area, and thus the separate attaching of the reference markers may be omitted.

Meanwhile, the splint 80 may be manufactured by being three-dimensionally printed to protrude from a tooth implanting portion area surface s of the primarily scanned image 311 to an outside. Here, the splint 80 is manufactured so that an inner surface thereof includes marker grooves 81 which correspond to the tooth implanting portion and are matched with the reference markers 40. The reference markers 40 are inserted into the marker grooves 81 of the splint 80, and the occlusal base is stacked on an outer surface of the splint 80 facing the opposing tooth (s320).

Here, it may be understood that the splint is a fixing unit which is provided to substantially fix the reference markers 40 to the outer surface of the gum of the tooth implanting portion having the high movability.

Specifically, the primarily scanned image 311 includes a three-dimensional image of the outer surface of the first impression model 110 including an image of the tooth implanting portion and the reference markers 40. The tooth implanting portion area surface s corresponding to the tooth implanting portion is set from the primarily scanned image 311. Here, the tooth implanting portion area surface s may be set by designating a certain area on the primarily scanned image 311. Of course, if necessary, the tooth implanting portion area surface s may be set by automatically calculating an image corresponding to the tooth implanting portion in the computer.

Here, the splint 80 may be designed to protrude from the set tooth implanting portion area surface s to the outside. At this time, a portion set as the tooth implanting portion area surface s may be formed later as a third image matching groove 80*a* of the splint 80.

Specifically, the tooth implanting portion area surface s, which is indicated in the primarily scanned image 311 to protrude, may be designed to be replaced by the third image matching groove 80*a* formed to be concave inward. The designed splint 80 may be three-dimensionally printed, and thus the splint 80 having the third image matching groove 80*a* which is matched with the tooth implanting portion may be manufactured.

At this time, in the manufactured splint 80, the marker grooves 81 matched with the reference markers 40 are formed at an inside of the third image matching groove 80*a*. Here, the splint 80 may be set to have a thickness which does not obstruct an occlusion of the upper and lower jaws, while installed at the tooth implanting portion, and then may protrude. The thickness may be about 1.8 to 2.2 mm.

The reference markers 40 are inserted into the marker grooves 81, and then the splint 80 is installed at the inside of the patient's mouth so that the third image matching groove 80*a* is matched with the outer surface of the patient's tooth implanting portion.

Here, the splint 80 may be formed of a radioparent material which is not indicated in a CT image 314 obtained through the CT scanning, and the reference markers 40 may be formed of a radiopaque material to be indicated on the CT image 314. Consequently, only an image of the alveolar bone of the tooth implanting portion and the reference markers 40, except the splint 80 and soft tissues like the gum through which radiation penetrates, may be indicated on the CT image 314.

At this time, the splint 80 is manufactured based on the primarily scanned image 311 obtained through the scanning of the first impression model 110 manufactured corresponding to the tooth implanting portion. Therefore, the marker grooves 81 correspond to positions of the reference markers 40 attached to the first impression model 110. Thus, the image of the reference markers 40 indicated on the primarily scanned image 311 may mutually correspond to the image of the positions of the reference markers 40 indicated on the CT image 314. Consequently, the image matching degree may be considerably improved by designating the positions of the reference markers 40 indicated on each image in the image matching process.

An occlusal base having a predetermined thickness is stacked on an outside of the splint 80. Here, the occlusal base may be stacked to have a thickness corresponding to a space between the opposing tooth and an upper surface of the splint 80, while the splint is installed at the tooth implanting portion and the upper and lower jaws are occluded. At this time, a basic structure of the occlusal base and a method for setting an occlusal height are the same as those of the second embodiment, and thus detailed description thereof will be omitted.

Meanwhile, while the splint 80 in which the occlusal height is set by adjusting the thickness of the occlusal base is installed at the patient's tooth implanting portion, the CT scanning is performed, and thus the CT image 314 considering the vertical dimension is obtained (s330).

Here, the CT image 314 includes the image of the reference markers 40 inserted into the marker grooves 81 of the splint. And since a shape of the opposing tooth and the alveolar bone of the tooth implanting portion, while the upper and lower jaws are occluded, are indicated three-dimensionally, the vertical dimension of the patient may be easily calculated from the CT image 314. At this time, the vertical dimension calculated from the CT image 314 may be applied later to a process in which a height of the crown is set.

Further, since the CT image is obtained while the splint 80 in which the occlusal base has the adjusted thickness suitable for the patient is installed at the tooth implanting portion and the upper and lower jaws are occluded, the reliability of the vertical dimension may be considerably improved.

Meanwhile, the splint 80 manufactured based on the primarily scanned image 311 by the manufacturer side is transferred to the operator side. And the transferred splint 80 is installed at the inside of the patient's mouth by the operator side, and the CT image 314 may be obtained through the CT scanning. Here, the occlusal base and the reference markers may be coupled to the splint 80 by the manufacturer side, and then may be transferred to the operator side. Of course, if necessary, the occlusal base and the reference markers may be coupled to the splint 80 by the operator side.

Meanwhile, the primarily scanned image 311 and the CT image 314 are overlapped with each other based on the reference markers 40, and matched with each other through the main matching process in a difference map from which the image matching degree between the images is output, and thus a three-dimensional occlusion guide image 315 is obtained (s340).

Specifically, three-dimensional exterior information of the tooth implanting portion and the reference markers 40 attached to the outside thereof may be obtained through the primarily scanned image 311. At this time, it may be understood that the three-dimensional exterior information is substantially exterior information of the first impression model 110 corresponding to the tooth implanting portion.

Two-dimensional and three-dimensional internal tissue information of the patient's mouth including the patient's upper and lower jaws, and image information of the reference markers 40 may be obtained through the CT image 314.

Here, since the image of the reference markers 40 is indicated at a mutually corresponding position between the primarily scanned image 311 and the CT image 314, the main matching process may be performed using the reference markers as the matching references. Therefore, the three-dimensional occlusion guide image 315 including the information obtained from the primarily scanned image 311 and the CT image 314 may be obtained. At this time, a process in which the three-dimensional occlusion guide image 315 is obtained is the same as that of the first embodiment, and thus detailed description thereof will be omitted.

Meanwhile, the secondarily scanned image may also be matched with the CT image 314 to obtain clearer shape information of the inside of the patient's mouth and thus to improve the accuracy of the dental implant.

At this time, an integrated scanned image obtained by aligning the primarily scanned image 311 with the secondarily scanned image according to an aligning reference mark between the first impression model 110 and the second impression model may be matched with the CT image 314.

Specifically, the primarily scanned image 311 and the secondarily scanned image may be first aligned with each other. Further, an occlusal scanned image obtained through the scanning of an occluded state of the first impression model 110 and the second impression model while the splint 80 is installed may be further provided to guide an accurate alignment between the primarily scanned image 311 and the secondarily scanned image.

At this time, the occlusal scanned image is obtained through the scanning of the occluded state of the first impression model 110 and the second impression model, while the splint 80 is installed at the outside of the first impression model 110.

Common portions between the primarily and secondarily scanned images and the occlusal scanned image are set as comparative areas for the aligning reference mark, and the primarily and secondarily scanned images and the occlusal scanned image are aligned. Here, since each scanned image is obtained based on the first impression model 110 and the second impression model, a similar portion at an outer surface of each impression model may be set as the comparative area.

For example, an outer end of the first impression model 110 commonly indicated on the primarily scanned image 311 and the occlusal scanned image may be set as the comparative area, and the alignment may be performed. And one side portion of the opposing tooth commonly indicated on the secondarily scanned image and the occlusal scanned image may be set as the comparative area, and the alignment may be performed. At this time, an unnecessary image such as the image of the splint 80 including the occlusal base may be removed from the occlusal scanned image to more accurately align the each scanned image.

When the primarily and secondarily scanned images are aligned and the occlusal scanned image is removed, the primarily and secondarily scanned images may be aligned corresponding to the vertical dimension calculated from the occlusal scanned image. Therefore, the integrated scanned image considering the vertical dimension may be obtained.

At this time, the integrated scanned image includes the image of the reference markers 40 provided from the primarily scanned image 311. Therefore, the CT image 314 and the integrated scanned image may be matched with each other using pairs of the matched reference markers 40 as the matching references. Therefore, the three-dimensional occlusion guide image 315 considering the exterior information of the inside of the patient's mouth and the vertical dimension.

At this time, the occlusal scanned image is obtained through the scanning of each impression model while the splint 80 is installed, and the CT image 314 is obtained through the CT scanning of the occluded state of the upper and lower jaws while the splint 80 is installed. Further, since the occlusal base having the set occlusal height is stacked on the outer surface of the splint 80, vertical dimension values calculated from the occlusal scanned image and the CT image 314 may corresponds to each other.

Here, in the CT image 314, an aligning impression portion may be formed at an upper surface of the occlusal base so that an occluded shape of the patient's upper and lower jaws substantially coincides with an occluded shape of the first impression model 110 and the second impression model.

Specifically, the aligning impression portion may be formed by hardening a curable impression resin coated on the upper surface of the occlusal base, which has the thickness adjusted to provide the proper occlusal height, in the process in which the occlusal height of the occlusal base is adjusted.

At this time, the splint 80 in which the curable impression resin is coated on the upper surface of the occlusal base is installed at the patient's tooth implanting portion, and then when the upper and lower jaws are occluded, a mastication mark of the opposing tooth may be formed in the form of a mastication groove at the aligning impression portion. That is, an end of an opposing tooth shape of the second impression model is restricted in the mastication groove formed at the aligning impression portion, and thus the first impression model 110 and the second impression model may be occluded at an accurate position.

Consequently, the vertical dimension values of the CT image 314 obtained through the CT scanning of the occluded state of the patient's upper and lower jaws and the occlusal scanned image obtained through the scanning of the occluded state of the first impression model 110 and the second impression model may correspond to each other.

Of course, if necessary, the primarily scanned image 311 and the secondarily scanned image may be matched with the CT image 314 using portions corresponding to the CT image 314 as the matching references.

Specifically, the matching process may be performed using the predetermined points of the reference markers 40, which are the common portions between the primarily scanned image 311 and the CT image 314, as the comparative areas. And the matching process may be performed using the predetermined points of the outside of the opposing tooth, which are the common portions between the secondarily scanned image and the CT image 314, as the comparative areas.

That is, after the primarily and secondarily scanned images are aligned in consideration of the vertical dimension, the primarily and secondarily scanned images may be matched with the CT image 314. Also, if necessary, each of the primarily scanned image 311 and the secondarily scanned image may be matched with the CT image 314, and such a modified example belongs to the range of the present invention.

Meanwhile, a height of the crown is set based on the three-dimensional occlusion guide image 315. At this time, the surgical guide including a fixing groove which is matched with the internal shape of the patient's mouth and a guide hole which is formed along the implanting position of the fixture corresponding to the set crown is manufactured (s240).

Here, the crown may be designed corresponding to the vertical dimension value based on the three-dimensional occlusion guide image.

Specifically, the vertical dimension value may be calculated from the CT image 314 obtained through the CT scanning of the occluded state of the upper and lower jaws while the splint 80 is installed. In addition, the shape of the masticating surface and the tooth arrangement state of the opposing tooth, and the exterior information of the upper and lower jaws may be obtained through the primarily scanned image 311 and the secondarily scanned image. By integrating such information, not only the height and the shape of the crown but also the implanting position of the implantation material much as the abutment, the crown and the fixture may be set on the three-dimensional occlusion guide image 315.

And the surgical guide is manufactured to include the fixing groove which is matched with the internal shape of the patient's mouth, and the guide hole which is formed along the implanting position of the fixture.

The surgical guide is designed from the exterior image of the tooth implanting portion included in the three-dimensional occlusion guide image 315 so that the fixing groove is substantially matched with the outer surface of the tooth implanting portion. Of course, the fixing groove may be obtained from the primarily scanned image 311 obtained through the scanning of the first impression model 110 corresponding to the tooth implanting portion. Further, the fixing groove may be designed from an internal shape of the splint 80 three-dimensionally printed from the primarily scanned image 311 to be substantially matched with the outer surface of the tooth implanting portion.

When the fixing groove is designed, a direction of the guide hole is set corresponding to the implanting direction of the fixture based on a state in which the surgical guide is fixed to the tooth implanting portion, and then the surgical guide may be manufactured.

Meanwhile, an image obtaining order in each embodiment may be elastically changed according to an operators' procedure style. For example, the CT image may be first obtained through the CT scanning, and then each scanned image may be obtained.

Through the above-described configuration, the method for manufacturing the surgical guide, and the crown and the abutment in the mouth for the dental implant provides the following effects.

First, each image can be easily obtained using the denture which is already manufactured in consideration of the patient's vertical dimension, the shape of the masticating surface, or the like, or the tray which takes the impression to manufacture the denture. Also, by just integrating the obtained information of each image, it is possible to receive the information which can simultaneously manufacture the implantation material and the surgical guide having the enhanced accuracy and reliability. Further, the exterior information of the tooth implanting portion may be easily calculated by reversing each image matching groove formed at the denture or the tray to be dimensionalized. Therefore, the number of patient's hospital visits and the operator's procedure processes can be reduced, and also the foundation technical device for the dental implant which completes the implanting and installing of the implantation material within a short period of time can be provided.

Second, even in the case of the edentulous patient to whom it is difficult to attach the reference markers as the matching reference points between the images, due to the high movability of the gum, since the reference markers are attached to the rigid outer surface of the denture or the tray, the obtained matching reference positions between the images can become clear. Consequently, since the accuracy of the surgical guide and the implantation material which are designed and manufactured based on the three-dimensional occlusion guide image obtained through the image matching process is improved, the reliability of the dental implant can be considerably enhanced.

Third, when the surgical guide is manufactured as the double guide, the first guide can be three-dimensionally printed based on the denture, and thus can be easily manufactured. Also, the second guide having the guide hole for guiding the implanting of the fixture is removably fastened to the opening of the first guide. Therefore, by just separating the second guide after the fixture is implanted, the abutment and the crown can be continuously fastened, even when the first guide is fixed to the tooth implanting portion.

Four, the splint which is three-dimensionally printed based on the primarily scanned image obtained through the scanning of the first impression model corresponding to the tooth implanting portion, and which has the marker grooves formed to be matched with the outer surface of the tooth implanting portion and allowing the reference markers to be inserted therein is installed at the tooth implanting portion, and thus the reference markers can be fixed to the gum having the high movability. Therefore, the reliability of the image matching reference using the reference markers indicated on each image can be considerably enhanced, and the accuracy of the surgical guide and the implantation material can be also enhanced, and thus the reliability of the dental implant can be remarkably improved.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method for manufacturing a surgical guide, and a crown and an abutment in a mouth for a dental implant, comprising:
    a first operation of obtaining a primarily scanned image through scanning of inner and outer surfaces of a denture which has a first image matching groove matched with a tooth implanting portion and in which a plurality of reference markers are attached to an outside thereof, obtaining a secondarily scanned image through oral scanning of upper and lower jaws while the denture is installed, preliminarily matching the secondarily scanned image with the primarily scanned image, obtaining an integrated scanned image by reversing the first image matching groove so that an image of the first image matching groove is dimensionalized from the primarily scanned image, and obtaining a CT image through CT scanning of the upper and lower jaws;
    a second operation of obtaining a three-dimensional occlusion guide image by overlapping the obtained integrated scanned image with the obtained CT image using the reference markers as references and matching the integrated scanned image and the obtained CT image in a main matching process in a difference map from which an image matching degree between the integrated scanned image and the obtained CT image is output; and
    a third operation of setting a height of a crown based on the three-dimensional occlusion guide image, and manufacturing a surgical guide including a fixing groove matched with an internal shape of the patient's mouth and a guide hole formed along an implanting position of a fixture corresponding to the set crown.

2. The method of claim 1, wherein the first operation comprises removing an image except an image of an inner surface profile of the first image matching groove and an image of the reference markers from the primarily scanned image, and performing a correction by reversing the inner surface profile of the first image matching groove to dimensionalize the image of the inner surface profile of the first image matching groove, extending a portion of the image of the reference markers, and connecting the extended portion of the image of the reference markers with an outer surface of a protruding shape of the first mage matching groove which is reversed.

3. The method of claim 1, wherein, when the integrated scanned image and the CT image are overlapped using the reference markers as the references and matched with each other through the main matching process in the difference map from which the image matching degree between the images is output, the second operation comprises setting common portions between the integrated scanned image and the CT image as comparative areas, and correcting each image so that uppermost portions and outermost portions of the comparative areas in the overlapped images coincide with each other.

4. The method of claim 1, wherein, in the first operation, the denture is installed at the tooth implanting portion and has an inner surface coated with a curable resin, and the first image matching groove is corrected with a profile formed corresponding to the tooth implanting portion formed at the curable resin.

5. The method of claim 1, wherein, in the third operation, a shape and an arrangement state of the crown is set based on the three-dimensional occlusion guide image including shape information of an artificial tooth portion of the denture obtained from the primarily scanned image.

6. The method of claim 1, wherein the second operation further comprises virtually arranging an imitation guide image, which is obtained by setting and removing an implanting area portion based on an artificial tooth boundary area of the denture, at an outside of a protruding shape of the image of the first image matching groove which is reversed to be dimensionalized,
    wherein the artificial tooth boundary area of the denture is selected and input, corresponding to an implanting position of an implantation material in the primarily scanned image included in the three-dimensional occlusion guide image; and
    wherein in the third operation, the surgical guide is manufactured based on the imitation guide image, and the surgical guide is designed and three-dimensionally printed as a double guide including a first guide and a second guide.

7. The method of claim 6, wherein the implanting area portion is set by selecting and inputting a plurality of boundary points along a boundary line between an artificial tooth of the denture corresponding to the implanting position of the implantation material and a peripheral artificial tooth portion adjacent to the artificial tooth of the denture corresponding to the implanting position of the implantation material, and calculating a closed surface including a connection line between each boundary point and another adjacent boundary point.

8. The method of claim 6, wherein the first guide has the fixing groove matched with the tooth implanting portion, and an opening corresponding to the removed implanting area portion, and the second guide has a guide hole in which the implanting area portion is formed along the implanting position of the fixture to be dimensionalized and to be connected to the opening, and an aligning protrusion and an aligning image matching groove which guide an aligning and coupling process are designed to be formed at mutually opposed surfaces of the second guide and the opening of the first guide, respectively.

9. The method of claim 6, wherein a shape and an arrangement state of the crown is set based on the three-dimensional occlusion guide image including shape information of an artificial tooth portion of the denture obtained from the primarily scanned image, wherein the guide hole of the second guide is set based on the implanting position of the fixture, and wherein the implanting position of the fixture is set based on the shape and the arrangement state of the crown.

10. The method of claim 1, wherein the first operation further comprises obtaining an aligning piece having a body portion which is configured to be filled in a space between the denture and an opposing tooth to fill the space and guide an occlusal position when the upper and lower jaws are occluded while the denture is installed, wherein an outer surface of the body portion includes a matching portion corresponding to end shapes of the opposing tooth and the denture.

* * * * *